US012672763B2

(12) United States Patent
Sharon et al.

(10) Patent No.: US 12,672,763 B2
(45) Date of Patent: Jul. 7, 2026

(54) ROBOTIC MANIPULATION OF A SURGICAL TOOL HANDLE

(71) Applicants: Microbot Medical Ltd., Yokneam Illit (IL); Technion Research & Development Foundation Limited, Haifa (IL)

(72) Inventors: Simon Sharon, Zichron Yaacov (IL); Idan Boader, Carmiel (IL); Evgeny Kofman, Kiriat-Motzkin (IL); Eran Cohen, Kiryat-Tivon (IL); Eyal Morag, Tel Aviv (IL); Harel Gadot, Hingham, MA (US); Moshe Shoham, Haifa (IL)

(73) Assignees: Microbot Medical Ltd., Yokneam Illit (IL); Technion Research & Development Foundation Limited, Haifa (IL)

( * ) Notice: Subject to any disclaimer, the term of this patent is extended or adjusted under 35 U.S.C. 154(b) by 917 days.

(21) Appl. No.: 17/780,547

(22) PCT Filed: Nov. 26, 2020

(86) PCT No.: PCT/IL2020/051225
§ 371 (c)(1),
(2) Date: May 27, 2022

(87) PCT Pub. No.: WO2021/105998
PCT Pub. Date: Jun. 3, 2021

(65) Prior Publication Data
US 2023/0346495 A1      Nov. 2, 2023

Related U.S. Application Data

(60) Provisional application No. 63/082,508, filed on Sep. 24, 2020, provisional application No. 62/941,842, filed on Nov. 28, 2019.

(51) Int. Cl.
*A61B 1/00* (2006.01)
*A61B 17/00* (2006.01)
(Continued)

(52) U.S. Cl.
CPC .......... *A61B 1/00147* (2013.01); *A61B 34/30* (2016.02); *A61B 34/35* (2016.02);
(Continued)

(58) Field of Classification Search
CPC ......... A61B 34/35; A61B 34/37; A61B 34/74; A61B 2017/00477; A61B 2034/301; A61M 25/0113
See application file for complete search history.

(56) References Cited

U.S. PATENT DOCUMENTS 3,789,841 A   2/1974   Antoshkiw
5,571,072 A   11/1996   Kronner
(Continued)

FOREIGN PATENT DOCUMENTS

CA      2918879      1/2015
CN      101918073    12/2010
(Continued)

OTHER PUBLICATIONS

International Preliminary Report on Patentability Dated Jun. 9, 2022 From the International Bureau of WIPO Re. Application No. PCT/IL2020/051224. (10 Pages).
(Continued)

*Primary Examiner* — Carl H Layno
*Assistant Examiner* — Dhrasti Snehal Dalal

(57) ABSTRACT

An adaptor for coupling a proximal portion of an elongate surgical tool to a motorized robotic surgical device, the adaptor comprising: a recess shaped and sized for receiving a proximal portion of an elongate surgical tool; one or more movers positioned to contact and move a control component
(Continued)

of the proximal portion; and transmission coupling which couples the one or more movers to motorized transmission of the robotic surgical device.

18 Claims, 20 Drawing Sheets

(51) Int. Cl.

| | |
|---|---|
| *A61B 34/00* | (2016.01) |
| *A61B 34/30* | (2016.01) |
| *A61B 34/35* | (2016.01) |
| *A61B 34/37* | (2016.01) |
| *A61M 25/00* | (2006.01) |
| *A61M 25/01* | (2006.01) |
| *A61M 25/02* | (2006.01) |
| *A61M 25/09* | (2006.01) |
| *B25J 9/00* | (2006.01) |
| *B25J 9/10* | (2006.01) |

(52) U.S. Cl.

CPC .............. *A61B 34/37* (2016.02); *A61B 34/70* (2016.02); *A61M 25/0113* (2013.01); *A61M 25/09041* (2013.01); *B25J 9/0021* (2013.01); *B25J 9/102* (2013.01); *A61B 2017/00477* (2013.01); *A61B 2034/301* (2016.02); *A61M 2025/0042* (2013.01); *A61M 2025/0253* (2013.01)

(56) References Cited

U.S. PATENT DOCUMENTS

| | | | |
|---|---|---|---|
| 6,017,354 | A | 1/2000 | Culp et al. |
| 6,171,234 | B1 | 1/2001 | White et al. |
| 6,290,675 | B1 | 9/2001 | Vujanic et al. |
| 6,358,199 | B1 | 3/2002 | Pauker et al. |
| 6,726,675 | B1 | 4/2004 | Beyar |
| 7,615,042 | B2 | 11/2009 | Beyar et al. |
| 8,317,745 | B2 | 11/2012 | Kirschenman et al. |
| 8,423,182 | B2 | 4/2013 | Robinson et al. |
| 8,480,618 | B2 | 7/2013 | Wenderow et al. |
| 8,894,610 | B2 | 11/2014 | Macnamara et al. |
| 9,192,745 | B2 | 11/2015 | Bencteux et al. |
| 9,795,764 | B2 | 10/2017 | Pacheco et al. |
| 10,149,680 | B2 | 12/2018 | Parihar |
| 10,376,323 | B2 | 8/2019 | Farritor |
| 10,524,867 | B2 | 1/2020 | Kokish et al. |
| 10,537,713 | B2 * | 1/2020 | Kidd .................. A61M 25/0113 |
| 10,543,047 | B2 | 1/2020 | Yu |
| 10,820,952 | B2 | 11/2020 | Yu |
| 10,980,608 | B2 | 4/2021 | Scheib et al. |
| 2002/0133077 | A1 | 9/2002 | Edwardsen et al. |
| 2002/0177789 | A1 | 11/2002 | Ferry et al. |
| 2004/0254566 | A1 | 12/2004 | Picchi et al. |
| 2005/0021065 | A1 | 1/2005 | Yamada et al. |
| 2005/0197566 | A1 | 9/2005 | Strommer et al. |
| 2008/0097465 | A1 | 4/2008 | Rollins et al. |
| 2009/0247944 | A1 | 10/2009 | Kirschenman et al. |
| 2011/0028894 | A1 | 2/2011 | Foley et al. |
| 2011/0105954 | A1 | 5/2011 | Cohen et al. |
| 2011/0130718 | A1 | 6/2011 | Kidd et al. |
| 2012/0110824 | A1 | 5/2012 | Smith et al. |
| 2013/0123803 | A1 | 5/2013 | Kirschenman et al. |
| 2014/0243742 | A1 | 8/2014 | Pchcco et al. |
| 2014/0276647 | A1 | 9/2014 | Yu |
| 2014/0276935 | A1 | 9/2014 | Yu |
| 2014/0277333 | A1 | 9/2014 | Lewis et al. |
| 2014/0305993 | A1 * | 10/2014 | Timm .................... A61B 17/32 227/178.1 |
| 2014/0309659 | A1 | 10/2014 | Roh |
| 2015/0001968 | A1 | 1/2015 | Zirps |
| 2015/0094732 | A1 | 4/2015 | Pacheco et al. |
| 2015/0112362 | A1 | 4/2015 | Inoue et al. |
| 2015/0374956 | A1 | 12/2015 | Bogusky |
| 2016/0030709 | A1 | 2/2016 | Losordo et al. |
| 2016/0157941 | A1 * | 6/2016 | Anvari ................... A61B 34/70 279/143 |
| 2016/0361128 | A1 | 12/2016 | Sceber |
| 2017/0105804 | A1 | 4/2017 | Yu |
| 2018/0055588 | A1 | 3/2018 | Yanagihara et al. |
| 2018/0168751 | A1 * | 6/2018 | Yi ...................... A61M 25/0116 |
| 2018/0228557 | A1 | 8/2018 | Darisse et al. |
| 2019/0125397 | A1 | 5/2019 | Arnold et al. |
| 2019/0201120 | A1 | 7/2019 | Shelton, IV et al. |
| 2019/0223967 | A1 | 7/2019 | Abbott et al. |
| 2019/0328599 | A1 | 10/2019 | Mahoney |
| 2020/0146759 | A1 | 5/2020 | Schena et al. |
| 2020/0155245 | A1 | 5/2020 | Yu |
| 2020/0163726 | A1 | 5/2020 | Tanner et al. |
| 2020/0222668 | A1 | 7/2020 | Wenderow et al. |
| 2020/0281666 | A1 | 9/2020 | Gunn et al. |
| 2021/0236217 | A1 | 8/2021 | Sharon et al. |
| 2021/0251709 | A1 | 8/2021 | Sharon et al. |
| 2021/0282875 | A1 | 9/2021 | Sharon et al. |
| 2022/0071723 | A1 | 3/2022 | Sharon et al. |
| 2023/0009618 | A1 | 1/2023 | Sharon |
| 2023/0346495 | A1 | 11/2023 | Sharon et al. |
| 2024/0197415 | A1 | 6/2024 | Sharon et al. |
| 2024/0358448 | A1 | 10/2024 | Boader et al. |

FOREIGN PATENT DOCUMENTS

| | | |
|---|---|---|
| CN | 103442660 | 12/2013 |
| CN | 103599585 | 2/2014 |
| DE | 102004007935 | 5/2005 |
| EP | 1061990 | 9/2004 |
| EP | 2347785 | 7/2011 |
| IL | 123646 | 5/2010 |
| IT | 201800009380 | 4/2020 |
| JP | 2002-525182 | 8/2002 |
| JP | 2010-253168 | 11/2010 |
| JP | 2011-509763 | 3/2011 |
| JP | 2011-519678 | 7/2011 |
| JP | 2015-523148 | 8/2015 |
| JP | 2017-104581 | 6/2017 |
| KR | 10-2129337 | 7/2020 |
| WO | WO 99/45994 | 9/1999 |
| WO | WO 2019/070696 | 4/2019 |
| WO | WO 2019/173107 | 9/2019 |
| WO | WO 2019/195841 | 10/2019 |
| WO | WO 2019/203616 | 10/2019 |
| WO | WO 2020/072543 | 4/2020 |
| WO | WO 2021/011551 | 1/2021 |
| WO | WO 2021/011554 | 1/2021 |
| WO | WO 2021/065311 | 4/2021 |
| WO | WO 2021/105997 | 6/2021 |
| WO | WO 2021/105998 | 6/2021 |
| WO | WO 2021/105999 | 6/2021 |
| WO | WO 2022/224234 | 10/2022 |
| WO | WO 2023/007478 | 2/2023 |

OTHER PUBLICATIONS

International Preliminary Report on Patentability Dated Jun. 9, 2022 From the International Bureau of WIPO Re. Application No. PCT/IL2020/051225. (7 Pages).

International Preliminary Report on Patentability Dated Jun. 9, 2022 From the International Bureau of WIPO Re. Application No. PCT/IL2020/051226. (11 Pages).

International Search Report and the Written Opinion Dated Feb. 15, 2021 From the International Searching Authority Re. Application No. PCT/IL2020/051224. (24 Pages).

International Search Report and the Written Opinion Dated Feb. 18, 2021 From the International Searching Authority Re. Application No. PCT/IL2020/051226. (18 Pages).

International Search Report and the Written Opinion Dated Feb. 25, 2021 From the International Searching Authority Re. Application No. PCT/IL2020/051225. (14 Pages).

Interview Summary Dated Nov. 19, 2021 from Re. U.S. Appl. No. 17/233,774. (3 pages).

(56) References Cited

OTHER PUBLICATIONS

Interview Summary Dated Oct. 20, 2021 from Re. U.S. Appl. No. 17/331,837. (2 pages).
Invitation to Pay Additional Fees and Communication Relating to the Results of the Partial International Search Dated Jan. 12, 2021 From the International Searching Authority Re. Application No. PCT/IL2020/051224. (13 Pages).
Notice of Allowance Dated Nov. 12, 2021 together with Interview Summary from Re. U.S. Appl. No. 17/331,837. (11 pages).
Notice of Allowance Dated Aug. 20, 2021 from Re. U.S. Appl. No. 17/187,936. (7 pages).
Notice of Allowance Dated Dec. 22, 2021 from Rc. U.S. Appl. No. 17/233,774. (12 pages).
Official Action & Interview Summary Dated Sep. 2, 2021 From Re. U.S. Appl. No. 17/233,774. (23 Pages).
Official Action Dated Aug. 2, 2021 from Re. U.S. Appl. No. 17/331,837. (19 pages).
Official Action Dated Jun. 23, 2021 From Re. U.S. Appl. No. 17/187,936. (13 Pages).
Restriction Official Action Dated Jul. 16, 2021 from Re. U.S. Appl. No. 17/233,774. (5 pages).
International Preliminary Report on Patentability Dated Nov. 2, 2023 From the International Bureau of WIPO Re. Application No. PCT/IL2022/050303 (10 Pages).
Office Action and Search Report Dated Jun. 4, 2023 From the Israel Patent Office Re. Application No. 298418. (10 Pages).
Requisition by the Examiner Dated Dec. 19, 2023 From the Innovation, Science and Economic Development Canada, Canadian Intellectual Property Office Re. Applicaiton No. 3,159,753. (13 Pages).
Supplementary European Search Report and the European Search Opinion Dated Dec. 5, 2023 From the European Patent Office Re. Application No. 20891520.7. (11 Pages).
Official Action Dated Nov. 24, 2023 from Re. U.S. Appl. No. 17/526,060. (41 pages).
Supplementary European Search Report and the European Search Opinion Dated Nov. 7, 2023 From the European Patent Office Re. Application No. 20893145.1. (8 Pages).
Requisition by the Examiner Dated Oct. 25, 2023 From the Innovation, Science and Economic Development Canada, Canadian Intellectual Property Office Re. Application No. 3,161,955 with claims. (14 Pages).
Office Action Dated Aug. 30, 2023 From the Israel Patent Office Re. Application No. 300398. (5 Pages).
Invitation to Pay Additional Fees and Communication Relating to the Results of the Partial International Search Dated Oct. 27, 2022 From the International Searching Authority Re. Application No. PCT/IL2022/050756. (5 Pages).
International Search Report and the Written Opinion Dated Jul. 5, 2022 From the International Searching Authority Re. Application No. PCT/IL2022/050303. (19 Pages).
European Search Report and the European Search Opinion Dated Sep. 1, 2022 From the European Patent Office Re. Application No. 22168338.6. (9 Pages).
International Search Report and the Written Opinion Dated Dec. 1, 2022 From the International Searching Authority Re. Application No. PCT/IL2022/050756. (15 Pages).
Office Action Dated Jan. 11, 2024 From the Israel Patent Office Re. Application No. 297409. (6 Pages).
Office Action Dated Jan. 11, 2024 From the Israel Patent Office Re. Application No. 300398. (4 Pages).
Requisition by the Examiner Dated Aug. 15, 2024 From the Innovation, Science and Economic Development Canada, Canadian Intellectual Property Office Re. Application No. 3,159,753. (11 Pages).
International Preliminary Report on Patentability Dated Feb. 8, 2024 From the International Bureau of WIPO Re. Application No. PCT/IL2022/050756 (10 Pages).

Notice of Reasons for Rejection Dated Sep. 3, 2024 From the Japan Patent Office Re. Application No. 2022-530811. and its Translation Into English. (20 Pages).
Requisition by the Examiner Dated Jan. 17, 2024 From the Innovation, Science and Economic Development Canada, Canadian Intellectual Property Office Re. Application No. 3,161,864. (12 Pages).
Notice of Reason(s) for Rejection Dated Jul. 23, 2024 From the Japan Patent Office Re. Application No. 2022-528230 and Its Translation Into English. (20 Pages).
Requisition by the Examiner Dated Jan. 4, 2024 From the Innovation, Science and Economic Development Canada, Canadian Intellectual Property Office Re. Application No. 3,156,099. (16 Pages).
Official Action Dated Mar. 14, 2024 from Re. U.S. Appl. No. 17/526,060. (30 pages).
Supplementary European Search Report and the European Search Opinion Dated Jan. 12, 2024 From the European Patent Office Re. Application No. 20892205.4. (8 Pages).
Machine Translation Dated Jul. 24, 2024 of Notification of Office Action and Search Report Dated Jul. 16, 2024 From the State Intellectual Property Office of the People's Republic of China Re. Application No. 202080086796.0. (7 Pages).
Notice of Reason(s) for Rejection Dated Jul. 16, 2024 From the Japan Patent Office Re. Application No. 2022-530812 and Its Translation Into English. (29 Pages).
Notification of Office Action and Search Report Dated Jul. 16, 2024 From the State Intellectual Property Office of the People's Republic of China Re. Application No. 202080086796.0. (8 Pages).
Notification of Office Action and Search Report Dated May 10, 2024 From the National Intellectual Property Administration of the People's Republic of China Re. Application No. 202080092059.1 and Its Machine Translation Into English. (18 Pages).
Requisition by the Examiner Dated Apr. 25, 2024 From the Innovation, Science and Economic Development Canada, Canadian Intellectual Property Office Re. Application No. 3,161,955 with claims. (10 Pages).
Restriction Official Action Dated Apr. 25, 2024 from Re. U.S. Appl. No. 17/780,039. (10 pages).
English Summary Dated May 27, 2024 of Notification of Office Action and Search Report Dated May 10, 2024 From the National Intellectual Property Administration of the People's Republic of China Re. Application No. 202080092059.1. (2 Pages).
Notice of Allowance Dated May 30, 2024 from Re. U.S. Appl. No. 17/526,060. (5 pages).
Office Action Dated May 26, 2024 From the Israel Patent Office Re. Application No. 298418. (5 Pages).
Restriction Official Action Dated May 30, 2024 from Re. U.S. Appl. No. 17/780,039. (6 pages).
Notification of Office Action and Search Report Dated Oct. 8, 2024 From the State Intellectual Property Office of the People's Republic of China Re. Application No. 202080094557.X and its Machine Translation. (15 Pages).
Official Action Dated Oct. 23, 2024 From Re. U.S. Appl. No. 17/780,039. (71 Pages).
Summary Dated Oct. 30, 2024 of Notification of Office Action Dated Oct. 8, 2024 From the State Intellectual Property Office of the People's Republic of China Re. Application No. 202080094557.X. (4 Pages).
Notification of Office Action and Search Report Dated Nov. 7, 2024 From the National Intellectual Property Administration of the People's Republic of China Re. Application No. 202080092059.1 and ItsSummary Translation Into English. (4 Pages).
Notice of Reason(s) for Rejection Dated Jan. 14, 2025 From the Japan Patent Office Re. Application No. 2022-530812 and Its Translation Into English. (13 Pages).
Office Action Dated Feb. 18, 2025 From the Israel Patent Office Re. Application No. 293370. (5 Pages).
Requisition by the Examiner Dated May 22, 2025 From the Innovation, Science and Economic Development Canada, Canadian Intellectual Property Office Re. Application No. 3,161,955. (4 Pages).

(56)           References Cited

OTHER PUBLICATIONS

English Summary Dated Aug. 5, 2024 of Notification of Office
Action Dated Jul. 16, 2024 From the State Intellectual Property
Office of the People's Republic of China Re. Application No.
202080086796.0. (2 Pages).
Office Action Dated Feb. 26, 2026 From the Israel Patent Office Re.
Application No. 293370. (6 Pages).

\* cited by examiner

1023

1021

1025

1117

1121

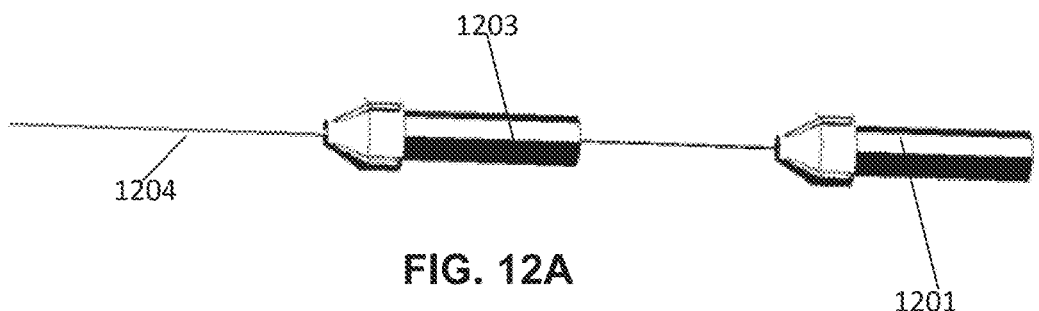
FIG. 12A
FIG. 12B
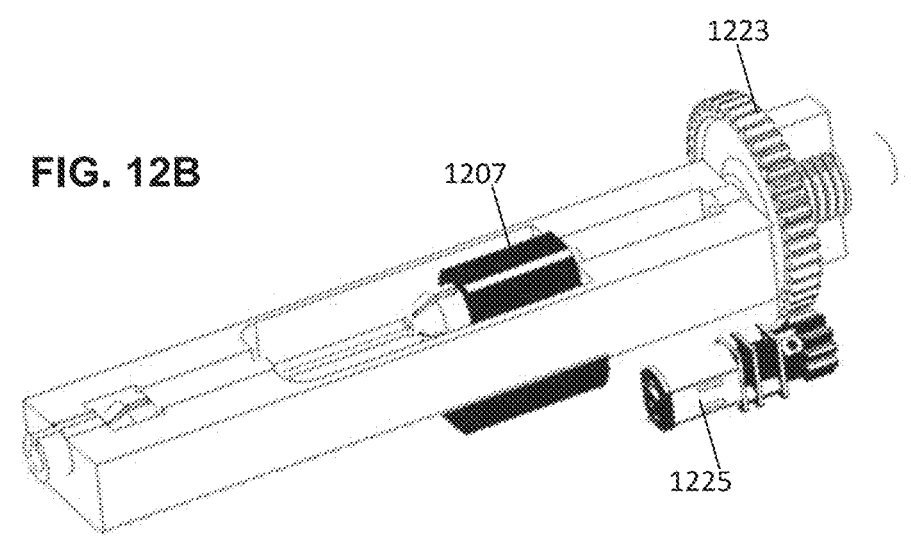
FIG. 12C
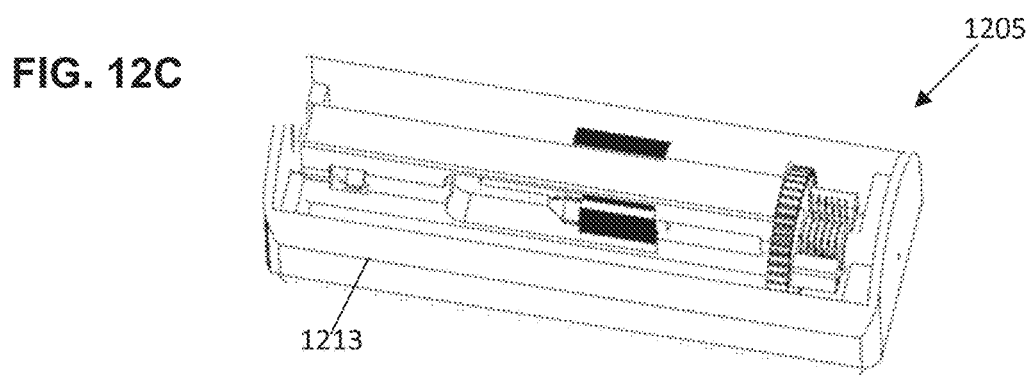

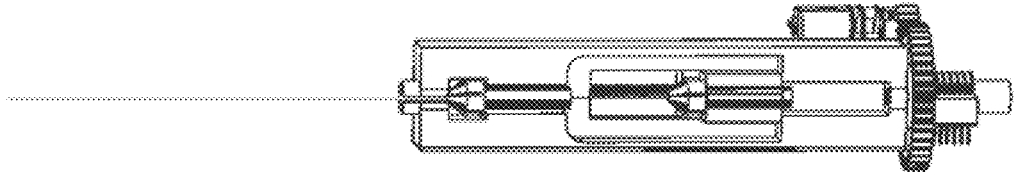
FIG. 12D
FIG. 12E
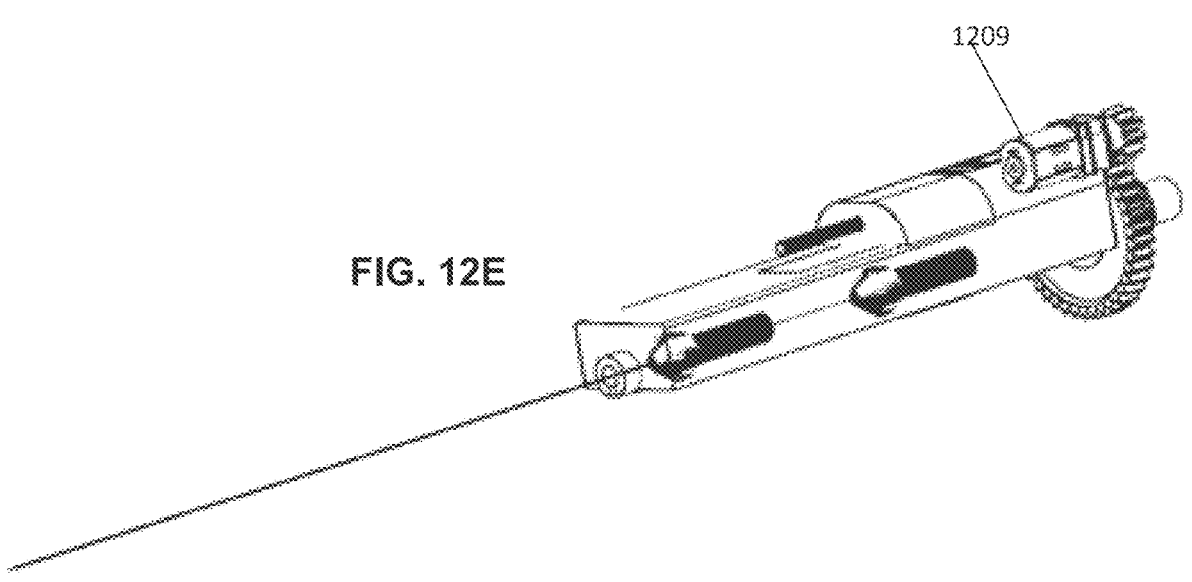

1401

1400

1403

1405

1407

ROBOTIC MANIPULATION OF A SURGICAL TOOL HANDLE

RELATED APPLICATION/S

This application a is National Phase of PCT Patent Application No. PCT/IL2020/051225 having International filing date of Nov. 26, 2020, which claims the benefit of priority under 35 USC § 119(e) of U.S. Provisional Patent Application No. 62/941,842 filed on Nov. 28, 2019, and of U.S. Provisional Patent Application No. 63/082,508 filed on Sep. 24, 2020. The contents of the above applications are all incorporated by reference as if fully set forth herein in their entirety.

PCT Patent Application No. PCT/IL2020/051225 filed on Nov. 26, 2020 is also related to co-filed, co-pending and co-assigned PCT application No. PCT/IL2020/051226 titled "DEVICE FOR AUTOMATICALLY INSERTING AND ADVANCING A MEDICAL TOOL INTO A BODILY LUMEN" and PCT application No. PCT/IL2020/051224 titled "MODULAR ROBOTIC SYSTEM FOR DRIVING MOVEMENT OF SURGICAL TOOLS" the contents of which are incorporated herein by reference in their entirety.

FIELD AND BACKGROUND OF THE INVENTION

The present invention, in some embodiments thereof, relates to motorized actuation of a surgical tool, and, more particularly, but not exclusively, to motorized manipulation of a proximal handle portion of an elongate endoluminal tool.

U.S. Pat. No. 10,543,047 discloses "A robotic instrument driver for elongate members includes a first elongate member, and at least one manipulator mechanism configured to manipulate the first elongate member, and at least one articulating drive configured to articulate the first elongate member, positionable on a bed and beside a patient access site. The manipulator and articulating drive are positioned relative to each other a distance less than the insertable length of the first elongate member, stationary in position."

SUMMARY OF THE INVENTION

According to an aspect of some embodiments there is provided an adaptor for coupling a proximal portion of an elongate surgical tool to a motorized robotic surgical device, the adaptor comprising:

a recess shaped and sized for receiving a proximal portion of an elongate surgical tool;

one or more movers positioned to contact and move a control component of the proximal portion; and transmission coupling which couples the one or more movers to motorized transmission of the robotic surgical device.

In some embodiments, a contour of the recess matches at least a portion of an external contour of the proximal portion of the tool, the recess sized to allow for axial rotation of the proximal portion and restrict lateral movement of the proximal portion when the proximal portion is within the recess.

In some embodiments, each of the one or more movers is independently actuated via the transmission coupling.

In some embodiments, the adaptor comprises a housing in which the recess is defined and which includes the one or more movers and the transmission coupling.

In some embodiments, at least an inner portion of the adaptor in which the recess is defined is configured to rotate along with the proximal portion of the tool.

In some embodiments, the one or more movers include an indentation formed in the recess, the indentation shaped and sized to fit onto a control component of the proximal portion of the tool.

In some embodiments, the transmission coupling is configured radially externally to the recess.

In some embodiments, the proximal portion is comprised of a handle, and wherein the control component, when moved, affects at least a distal portion of the elongate surgical tool.

In some embodiments, at least a portion of the housing is configured to slide linearly with respect to a body of the handle, along at least a portion of the length of the body.

In some embodiments, the control component is from the group of: an axial slider, a lock, a rotatable knob.

In some embodiments, the transmission coupling comprises an attachment to a lead screw, pin or rod which is driven by the motorized transmission of the robotic device.

In some embodiments, the housing comprises one or more motors which actuate the one or more movers.

In some embodiments, the housing is configured to be rotated as single unit about a long axis of the recess.

In some embodiments, the recess and the one or more movers are configured to rotate while the transmission coupling remains stationary.

In some embodiments, the housing comprises mechanical and/or electrical connections positioned and configured to attach to a housing of the robotic surgical device.

In some embodiments, the adaptor comprises a clutch which disengages the one or more movers from the transmission coupling.

In some embodiments, the adaptor comprises at least one sensor configured for indicating a relative position of the one or movers.

In some embodiments, the at least one sensor comprises an optical encoder.

According to an aspect of some embodiments there is provided an assembly comprising: an adaptor for example as described herein, and an elongate surgical tool comprising a proximal portion which is engaged by the adaptor.

In some embodiments, the proximal portion is removably received within the recess of the adaptor.

In some embodiments, the elongate surgical tool comprises a guidewire.

In some embodiments, the elongate surgical tool comprises a microcatheter.

According to an aspect of some embodiments there is provided a method of operably coupling a proximal manipulator of an elongate surgical tool to a motorized robotic surgical device, comprising:

providing a robotic surgical device for controlling and navigating at least one elongate surgical tool;

providing an adaptor configured for coupling between control components of the proximal manipulator of the elongate surgical tool to motorized transmission of the robotic surgical device;

aligning the control components of the manipulator relative to the adaptor; and coupling the adaptor to motorized transmission of the robotic surgical device.

In some embodiments, the method comprises actuating the motorized transmission of the robotic surgical device for moving, using the adaptor, the control components of the proximal manipulator, the control components generating at least one of: roll of the elongate surgical tool; deflection of a distal portion of the elongate surgical tool; a change in stiffness and/or size properties of the distal portion of the elongate surgical tool.

In some embodiments, moving comprises one or more of: sliding a slider component of the manipulator; rotating a rotating component of the manipulator; rotating the handle as a single unit.

In some embodiments, the method comprises selecting, out of a plurality of available adaptors, an adaptor which matches a geometry and function of a specific manipulator of a tool selected for use.

In some embodiments, the manipulator comprises a proximal handle of the tool.

According to an aspect of some embodiments there is provided a system comprising:

a robotic device configured for manipulation of at least one elongate surgical tool, the robotic device comprising one or more motors for actuating movement of the at least one elongate surgical tool; and an adaptor configured to operably attach to the robotic device, the adaptor comprising:

a first member shaped and configured for transferring movement actuated by the one or more motors of the robotic device, a second member shaped and configured to receive or fit onto at least a part of a proximal portion of the elongate surgical tool;

wherein movement of one or both of the first and second members, driven by the one or more motors of the robotic device, generates movement of at least a part of the proximal portion engaged by the adaptor.

In some embodiments, the robotic device comprises a controller configured to control movement of the first and second members of the adaptor for affecting at least a distal portion of the elongate surgical tool.

In some embodiments, the system further comprises a remote interface for controlling the controller.

In some embodiments, the adaptor comprises a plurality of movers which move components of the proximal portion, the movers driven by the one or more motors of the robotic device.

In some embodiments, a mover comprises one of: a mounting which is seated onto a sliding component of the proximal portion of the tool, a gear positioned to rotate a rotatable component of the proximal portion of the tool.

According to an aspect of some embodiments there is provided an adaptor for coupling a proximal handle of an elongate surgical tool to a motorized robotic surgical device, the adaptor comprising:

a first geometry shaped and sized for engaging a motor or motor transmission of the robotic surgical device;

a second geometry shaped and sized for engaging at least a portion of the proximal handle of the elongate surgical tool;

wherein the first geometry and the second geometry interface with each other such that movement of one of the geometries generates movement of at least one of: the other geometry or at least a portion of the proximal handle engaged by the adaptor.

In some embodiments, the first geometry and the second geometry are co-axial and wherein the first geometry is located peripherally to the second geometry.

In some embodiments, the second geometry defines at least one recess having a contour which matches at least a portion of an external contour of the proximal handle engaged by the adaptor.

In some embodiments, the recess is sized to surround at least part of a body of the proximal handle and to fittingly engage at least one component of the proximal handle which is integrally mounted onto the body of the proximal handle.

In some embodiments, the recess is shaped and sized to slide linearly with respect to the body of the handle, along at least a portion of the length of the body.

In some embodiments, the second geometry comprises at least one recess for receiving a motor transmission element of the surgical device, the motor transmission element comprising a lead screw, pin or rod which is driven by the motor or motor transmission of the robotic device.

In some embodiments, at least one of the first geometry and the second geometry is configured to rotate about a common axis of the first and second geometries.

In some embodiments, at least one of the first geometry and the second geometry is configured to slide axially.

In some embodiments, the first geometry and the second geometry are coupled to each other and wherein movement of one of the geometries causes similar movement of the other geometry.

In some embodiments, a coupling between the geometries comprises an interference fit coupling.

In some embodiments, a coupling between the geometries comprises at least a partial encasing of one of the geometries by the other geometry.

In some embodiments, the first and second geometries are formed as opposing faces of a single integral unit.

In some embodiments, the adaptor comprises a housing including the first and second geometries, the housing configured to be rotated as single unit about a long axis of the adaptor housing.

In some embodiments, the housing comprises mechanical and/or electrical connections positioned and configured to attach to a housing of the robotic surgical device.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 4A:
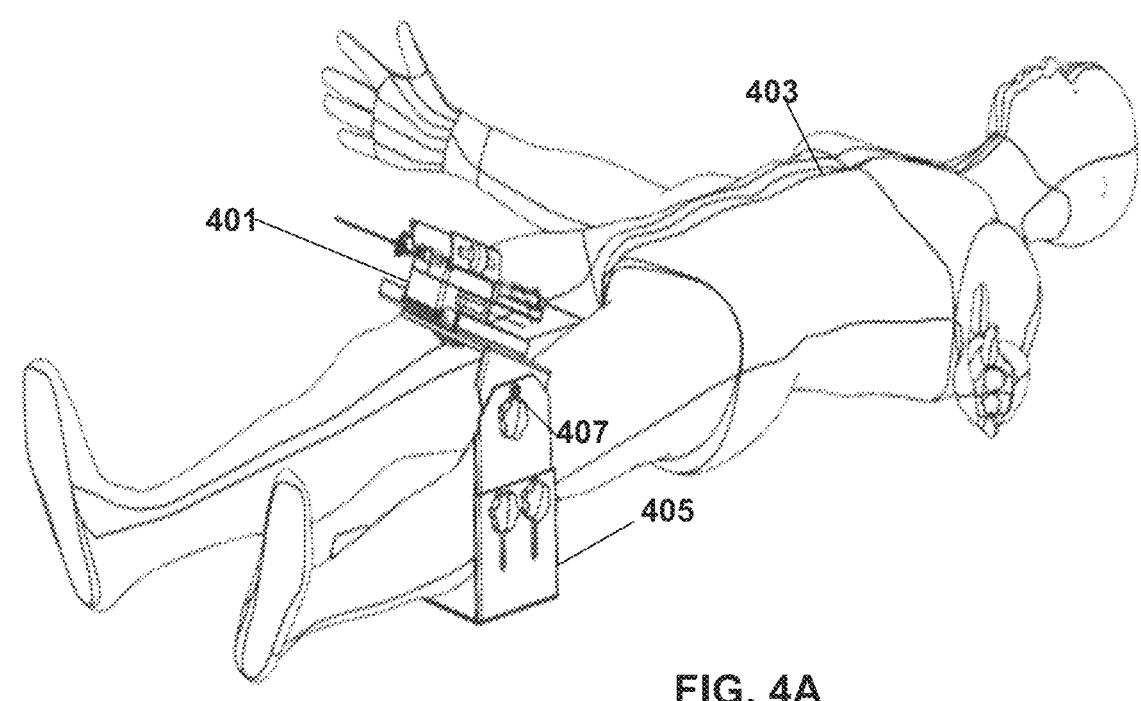
Figure 4B:
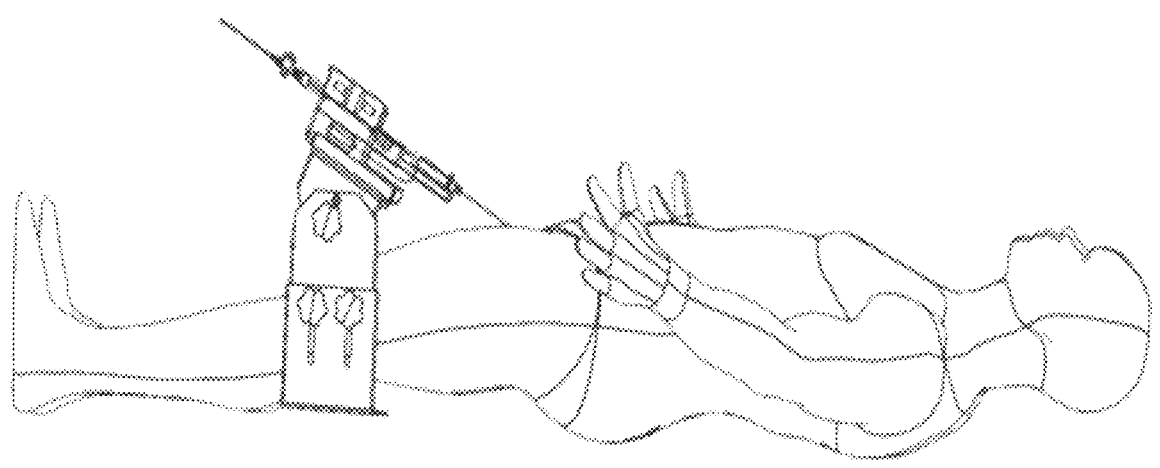
Figures 5A, 5B:
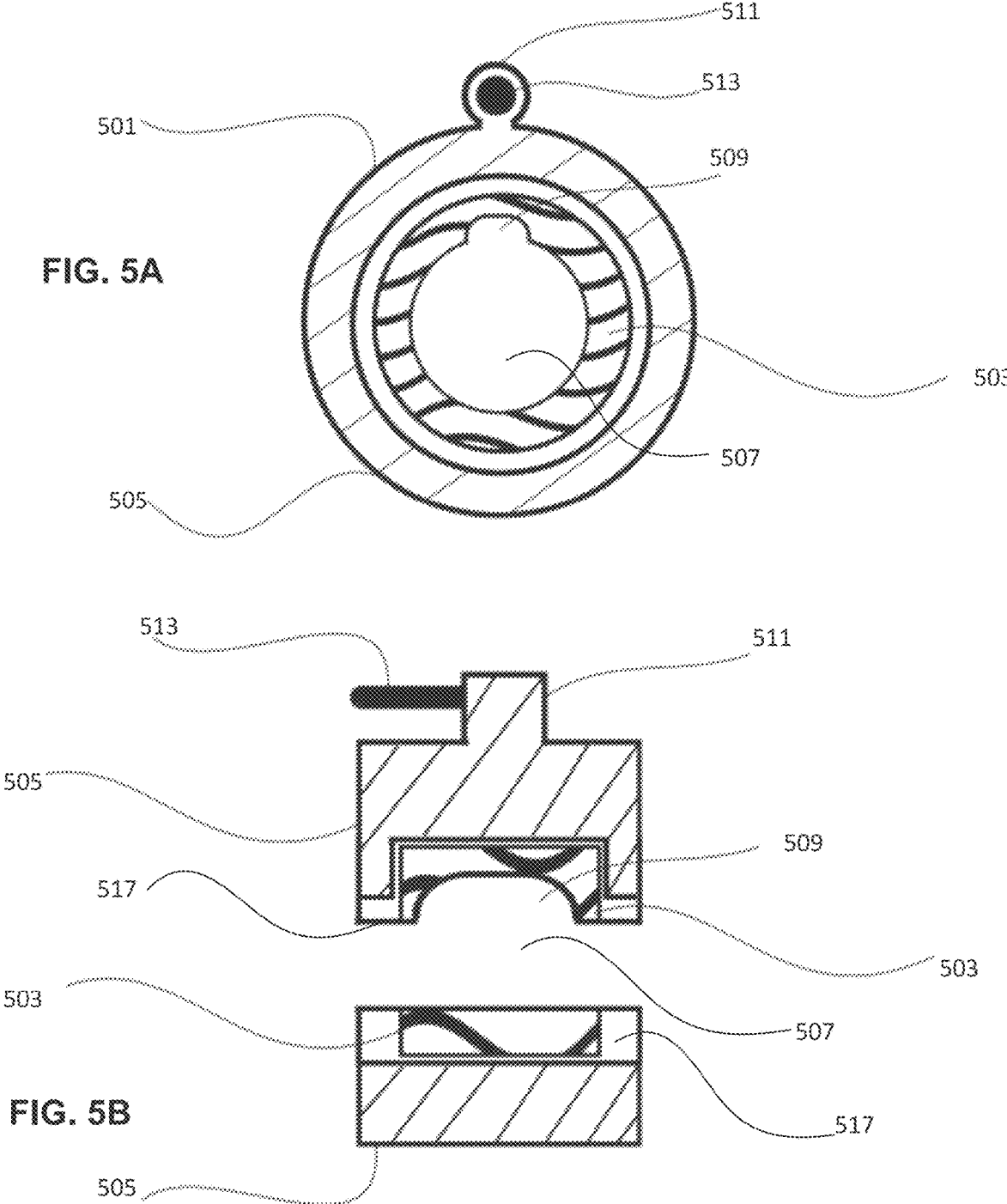
Figures 6A, 6B:
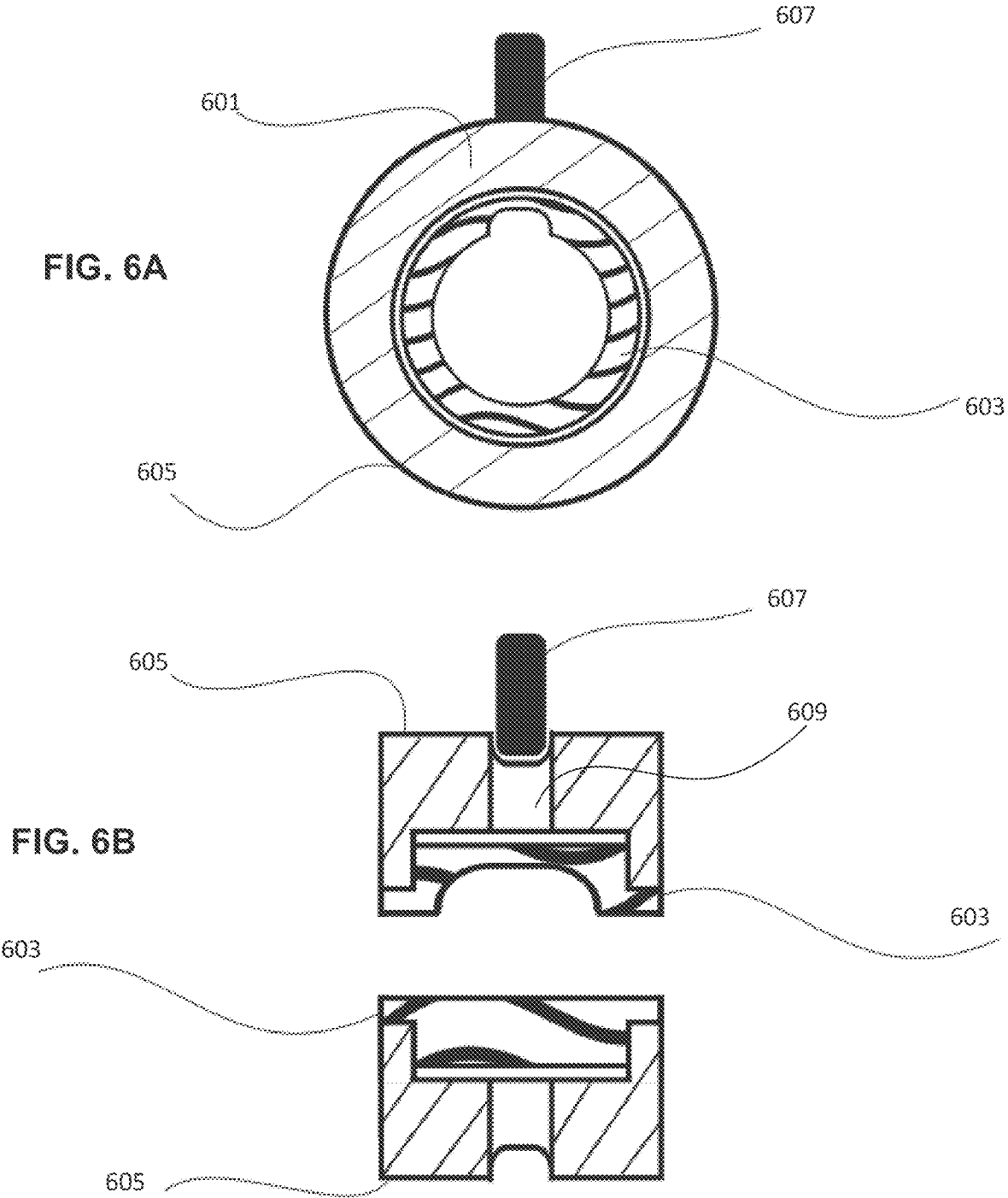
Figure 7A:
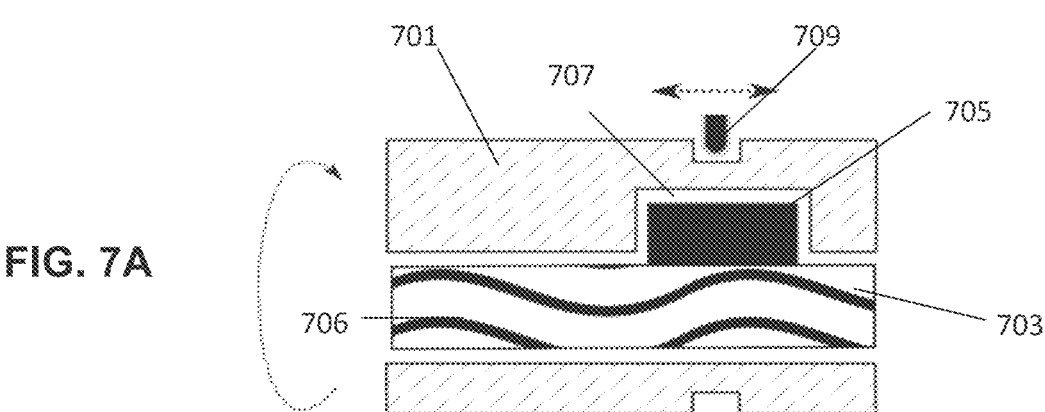
Figure 7B:
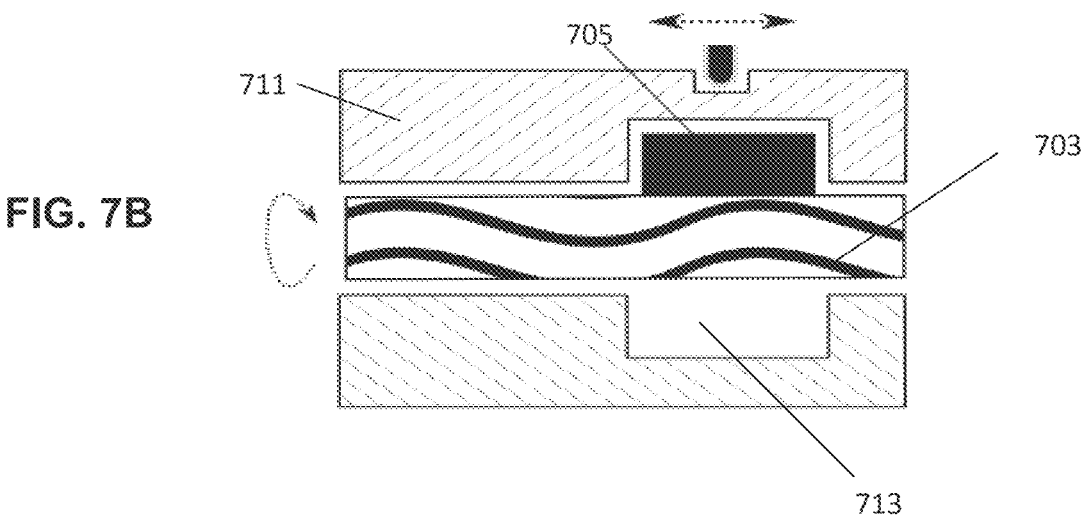
Figure 7C:
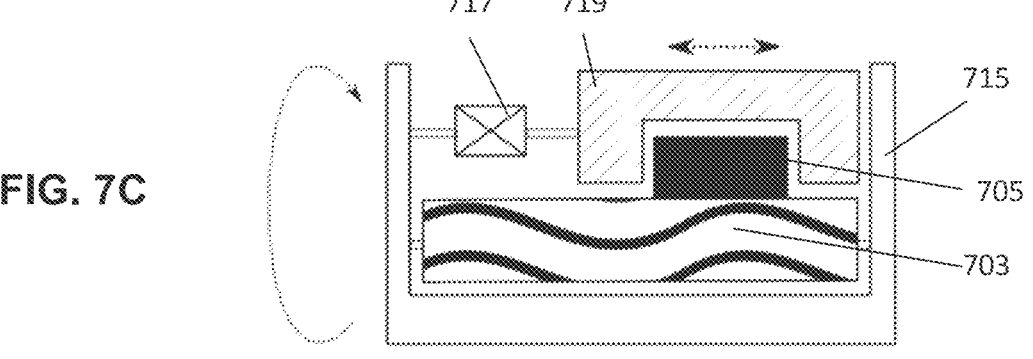
Figure 10A:
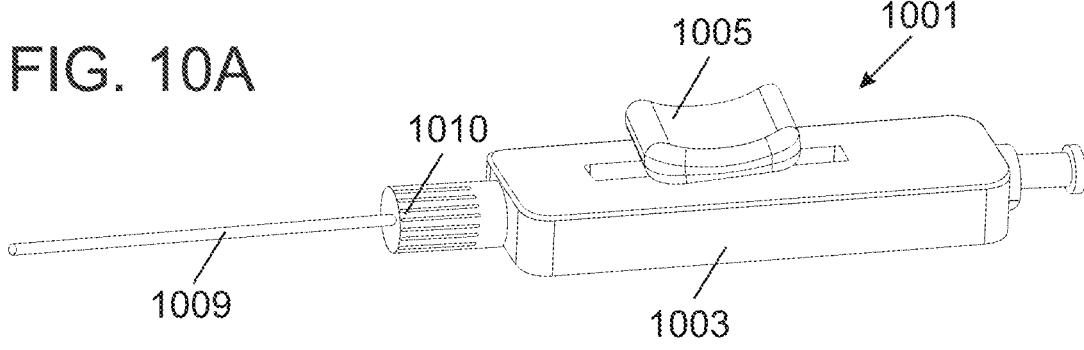
Figure 10B:
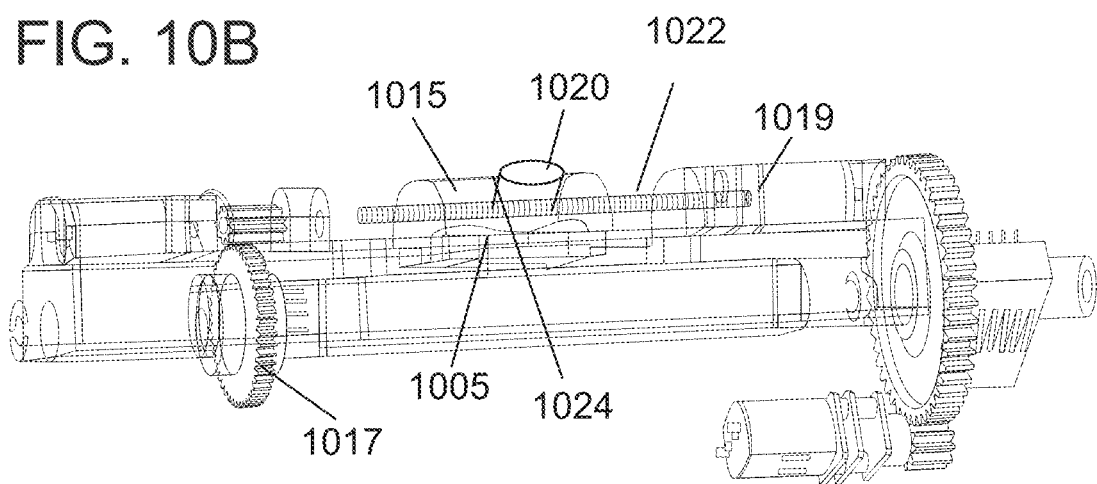
Figure 10C:
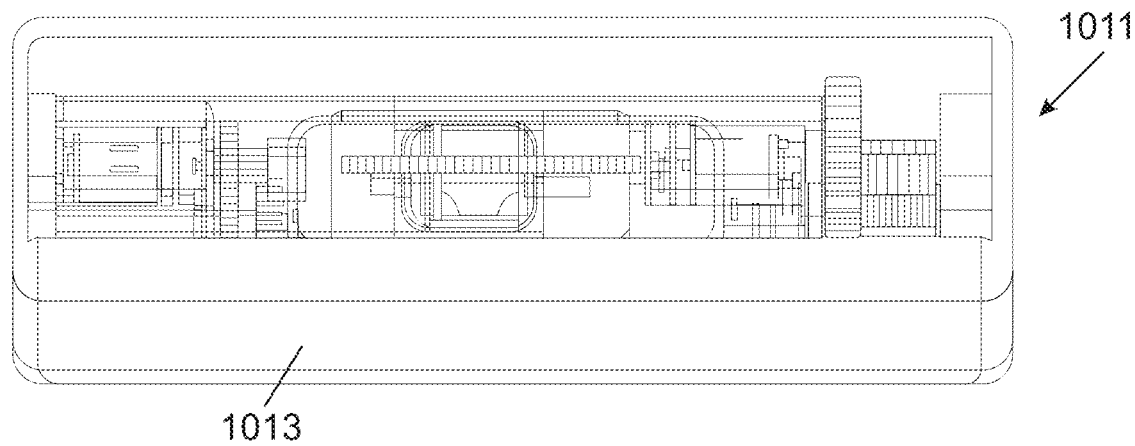
Figure 10D:
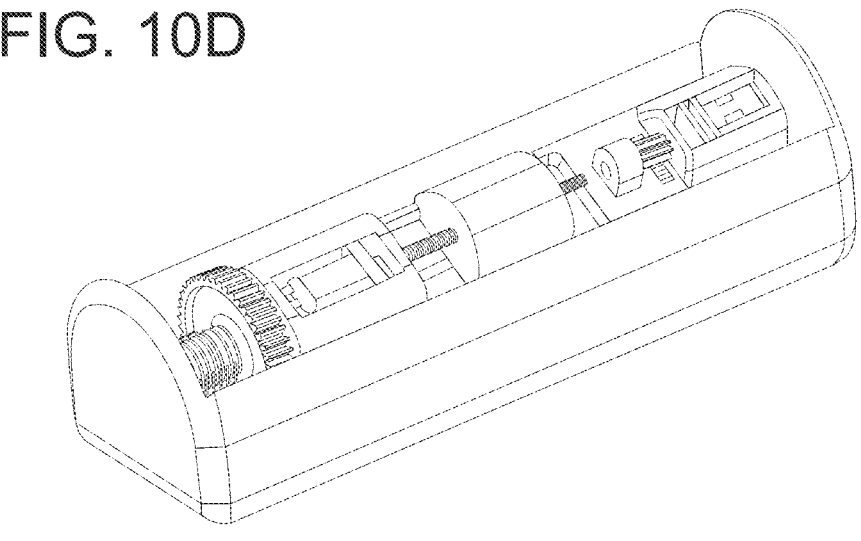
Figure 10E:
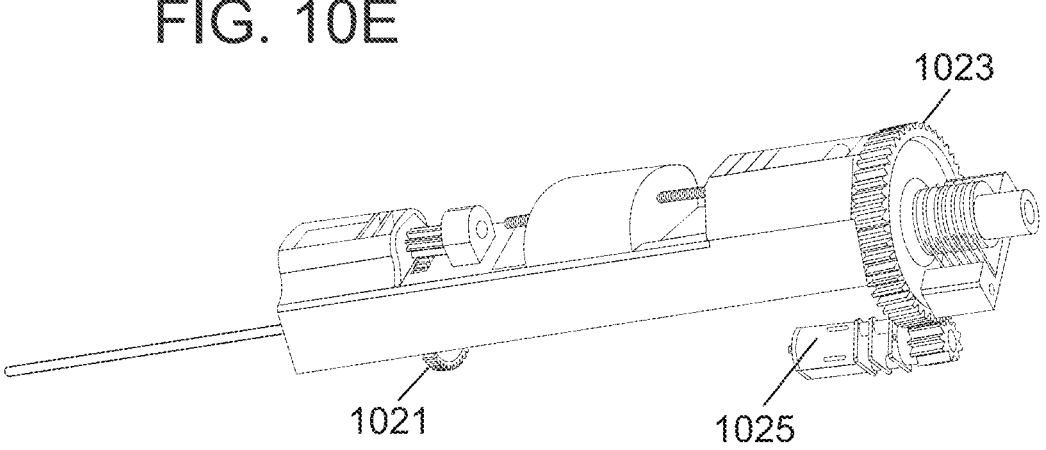
Figure 11A:
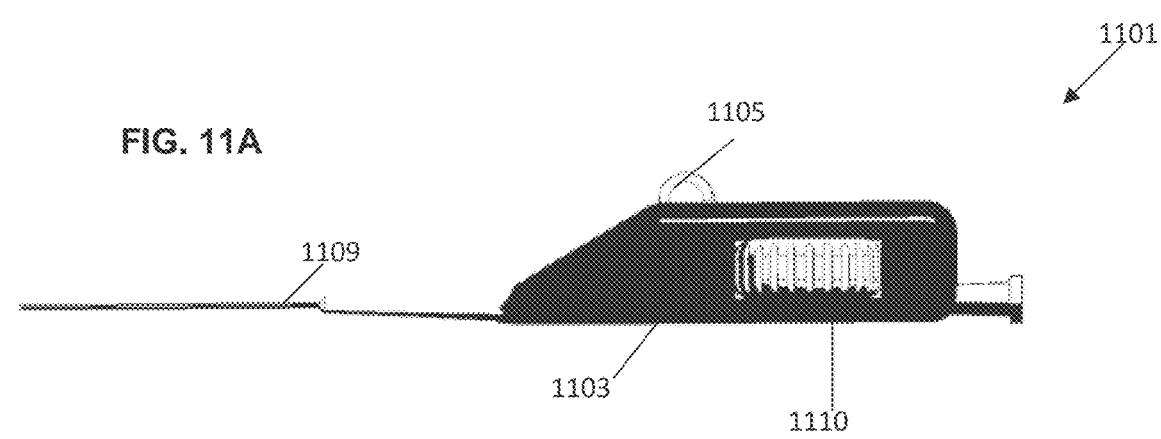
Figure 11B:
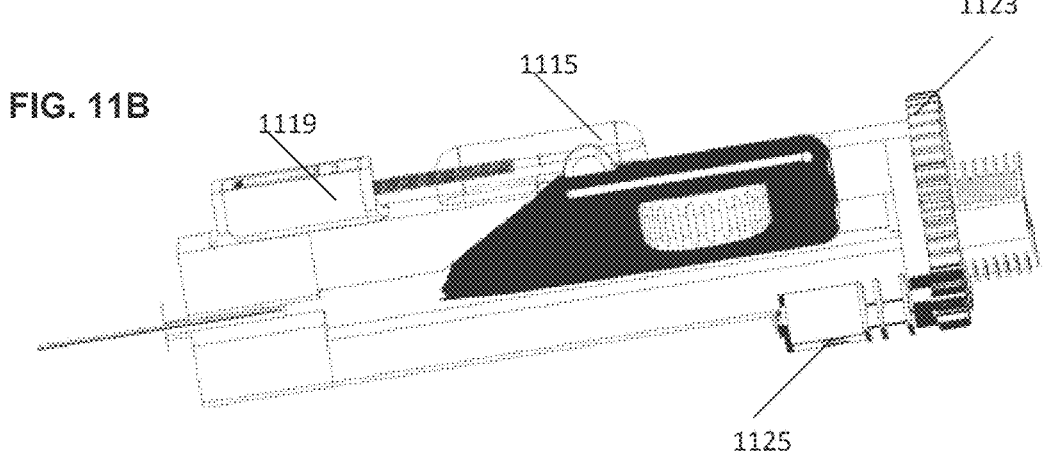
Figure 11C:
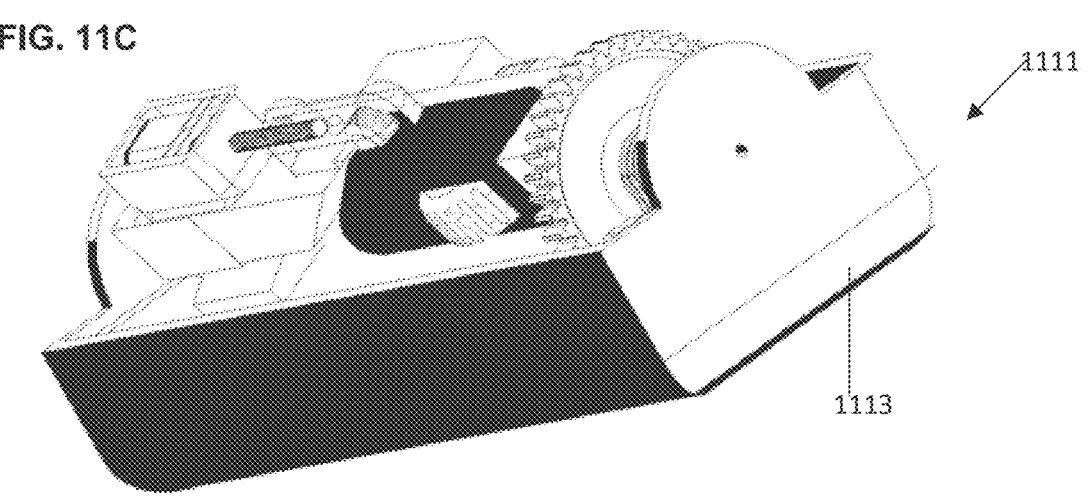
Figure 11D:
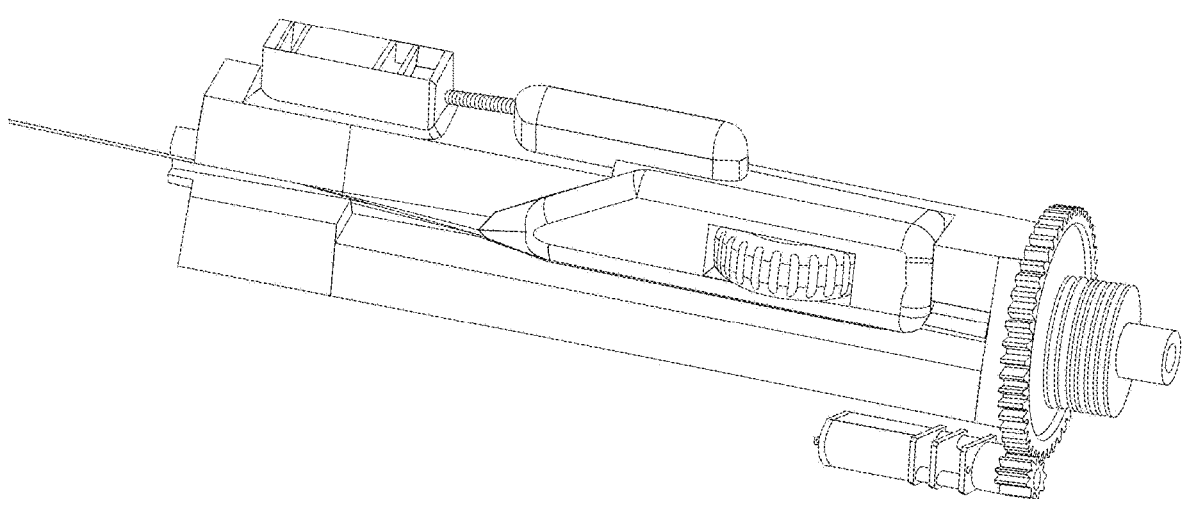
Figure 11E:
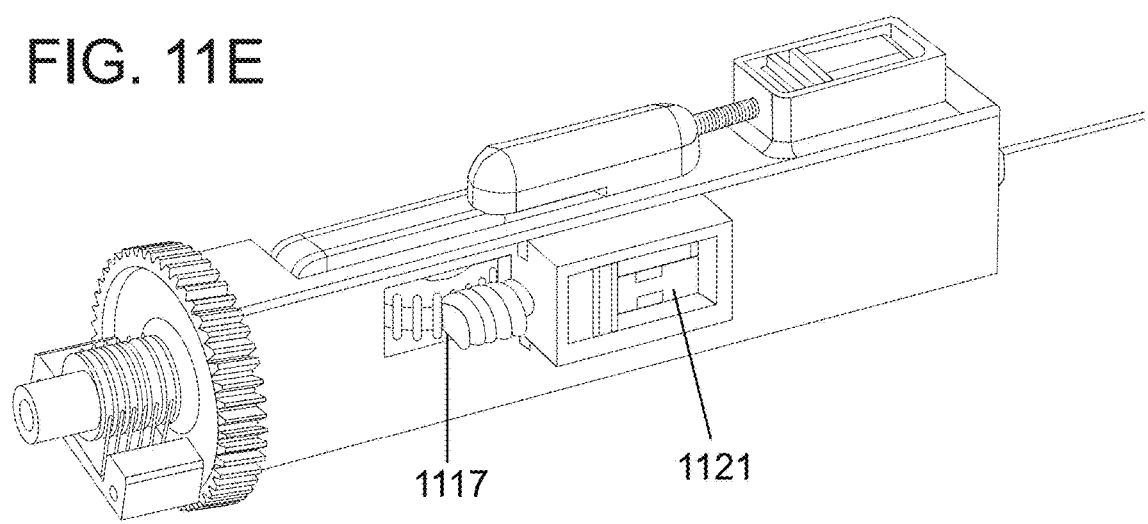
Figure 13A:
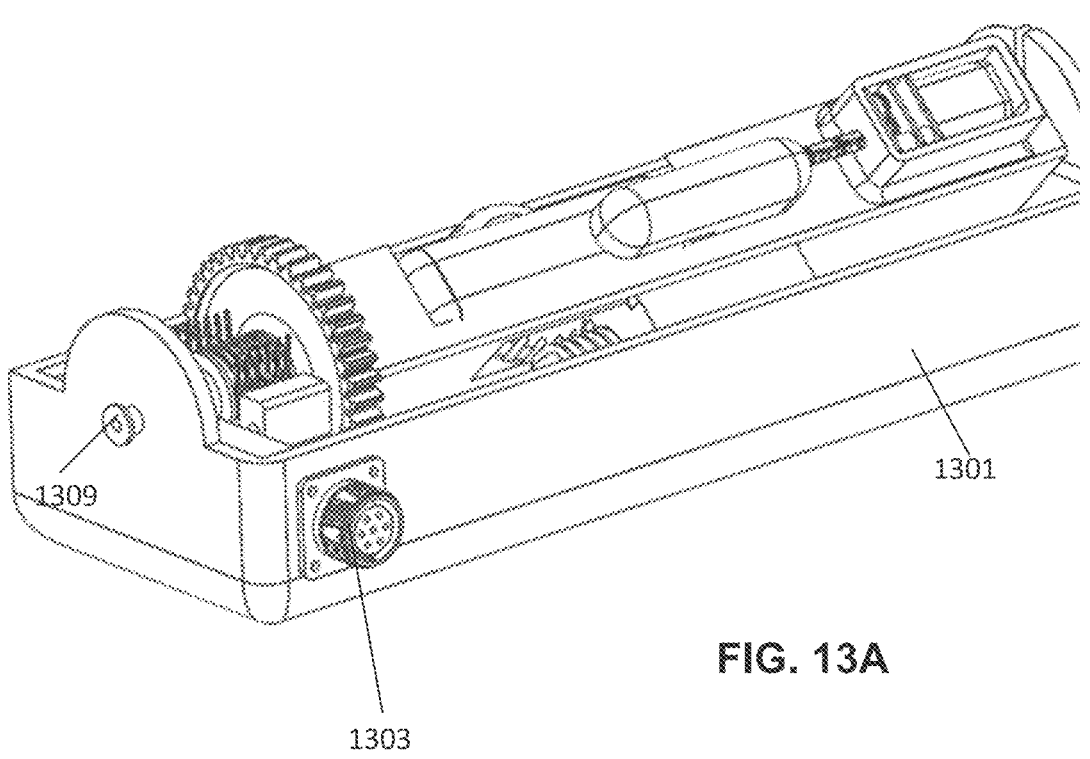
Figure 13B:
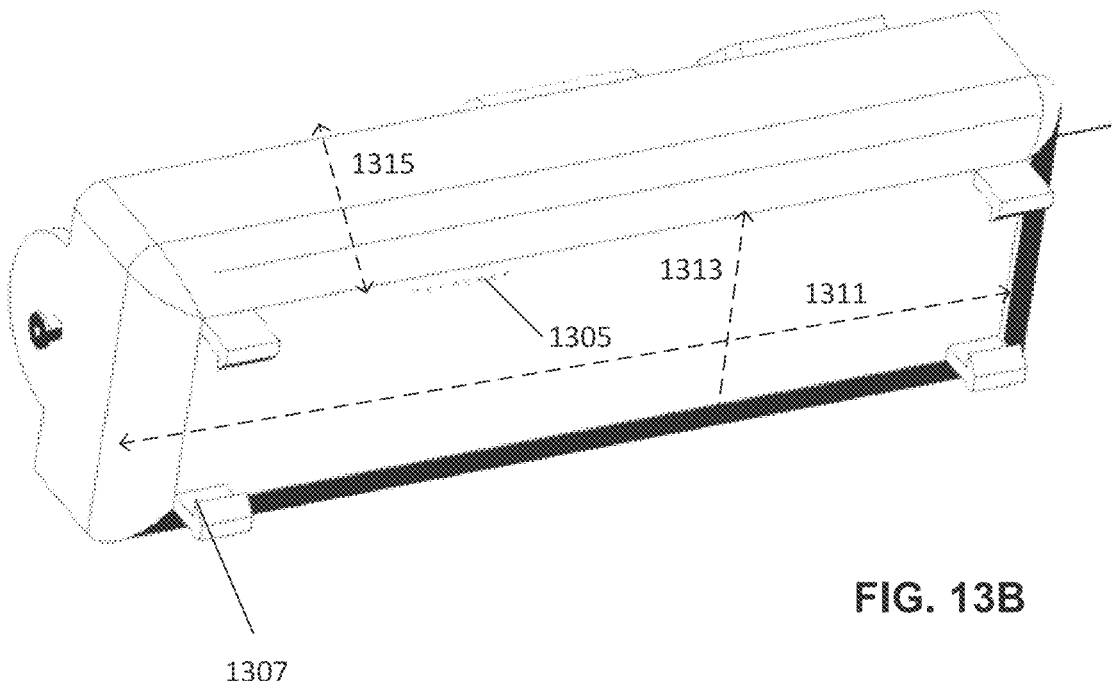
Figure 14:
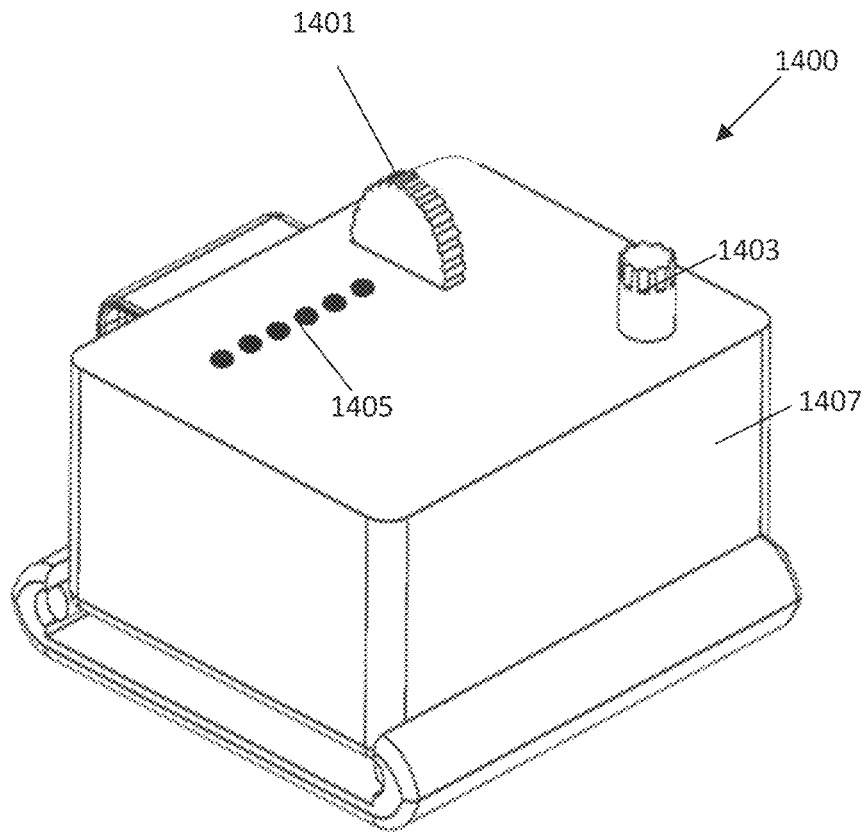
Figure 15:
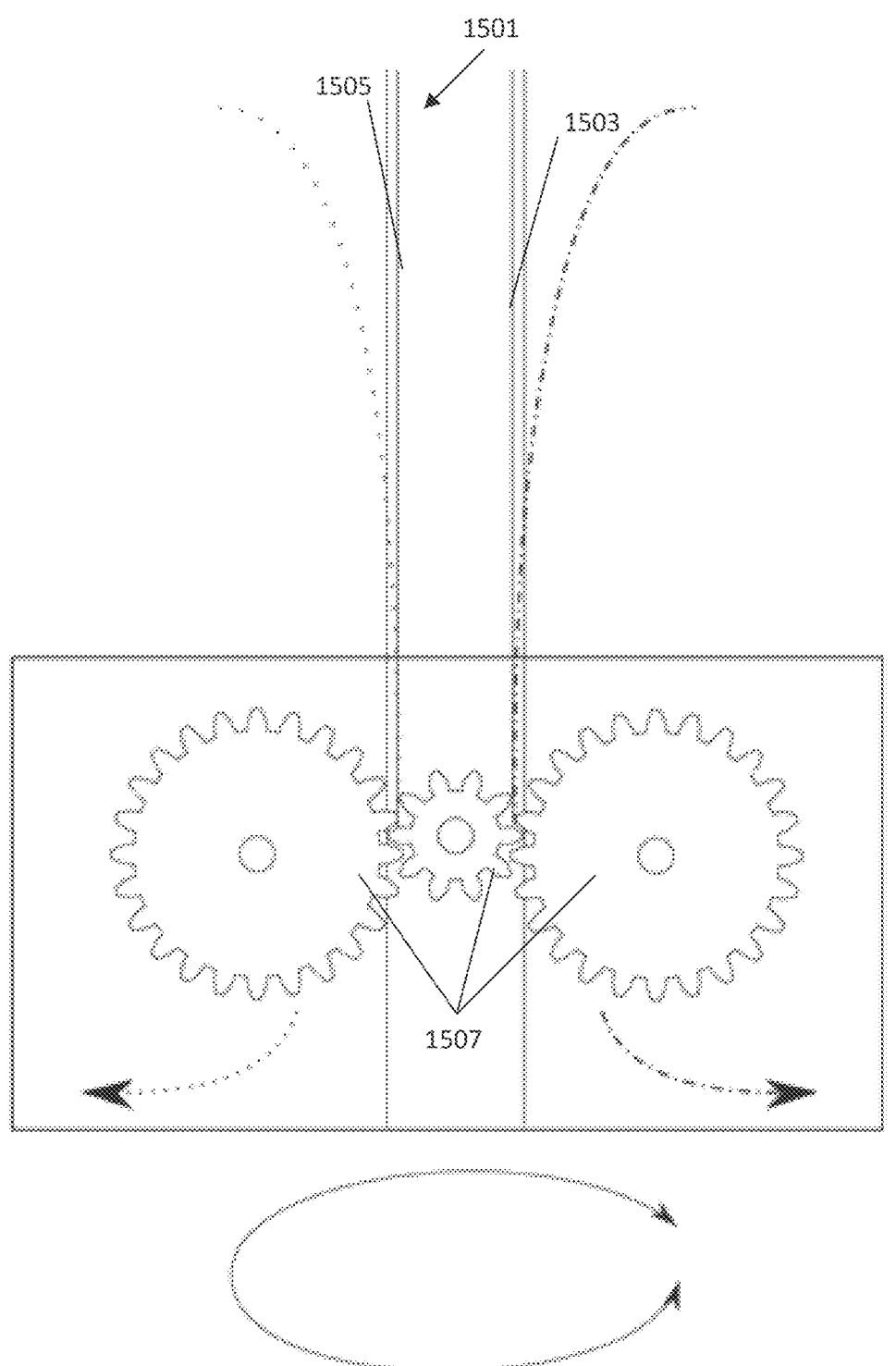

FIGS. 4A-B are an isometric view and a side view of a robotic surgical system positioned with respect to a patient, according to some embodiments;

FIGS. 5A-B are cross section views of an adaptor for coupling a proximal handle of an elongate surgical tool to a surgical robotic device, according to some embodiments;

FIGS. 6A-B are cross section views of an adaptor for coupling a proximal handle an elongate surgical tool to a surgical robotic device, according to some embodiments;

FIGS. 7A-C schematically show examples of alternative configurations of adaptors in which a handle of an elongate surgical tool is received, for coupling the handle to a surgical robotic device, according to some embodiments;

FIGS. 8A-F schematically show various positions of a handle of an elongate surgical tool within an adaptor for example as described in FIG. 7B, and a corresponding resulting effect on a distal end portion of the elongate surgical tool, according to some embodiments;

FIGS. 9A-D are isometric views (FIGS. 9A, 9C) and cross section views (FIGS. 9B, 9D) of exemplary mechanisms for engaging a proximal handle of an elongate surgical tool, according to some embodiments;

FIGS. 10A-E show a first example of a mechanism for engaging and actuating motorized movement of a guidewire handle as shown FIG. 10A, according to some embodiments;

FIGS. 11A-E show a second example of a mechanism for engaging and actuating motorized movement of guidewire handle as shown in FIG. 11A, according to some embodiments;

FIGS. 12A-E show a third example of a mechanism for engaging and actuating motorized movement of a proximal portion of a guidewire as shown in FIG. 12A (which does not have a proximal handle), according to some embodiments;

FIGS. 13A-B show a housing of an adaptor for engaging and actuating motorized movement of a handle of an elongate surgical tool, according to some embodiments;

FIG. 14 schematically illustrates a module of the surgical robotic device configured to operably engage an adaptor for coupling a proximal handle of an elongate surgical tool, according to some embodiments; and FIG. 15 schematically illustrates motor engagement of a proximal portion of a "double thread" guidewire, according to some embodiments.

DESCRIPTION OF SPECIFIC EMBODIMENTS OF THE INVENTION

The present invention, in some embodiments thereof, relates to motorized actuation of an elongate surgical tool, and, more particularly, but not exclusively, to motorized manipulation of a proximal portion of an elongate surgical tool, for example, of a handle of the tool or other proximal manipulator of the tool.

A broad aspect of some embodiments relates to robotic manipulation of a proximal portion of an elongate surgical tool. In some embodiments, a tool proximal portion (such as a manipulator or a handle commonly configured for manual operation) is operably attached to a robotic system which includes one or more motors for driving movement of the proximal portion of the tool and/or of selected components of this portion.

An aspect of some embodiments relates to an interface between a proximal portion of an elongate surgical tool, e.g. a guidewire and/or a microcatheter, and a robotic system configured for actuating movement of the tool. In some embodiments, the interface is in the form of an adaptor which is shaped and configured for operably coupling the proximal portion to one or more motors or motor transmission elements of the robotic system.

In some embodiments, the adaptor is configured to mechanically and/or electrically engage the proximal portion of the tool. In some embodiments, the adaptor includes a first geometry (also referred to herein as "first portion" or "first member") shaped and configured for interfacing with one or more elements (such as a screw gear, a rod, a gear wheel) of the robotic system which are configured to transfer motorized actuation force, and a second geometry (also referred to herein as "second portion" or "second member") shaped and configured for interfacing with the proximal portion of the tool.

In some embodiments, the first geometry comprises a transmission coupling, and the second geometry comprises one or more movers, which are actuated via the transmission coupling and are positioned to contact a control portion of the proximal portion, for example, contact control components of the proximal portion which upon movement actuate the tool. In some embodiments, a mover is comprised of a recess or an indentation (such as formed within inner walls of the adaptor) which comes in contact with a control component of the tool proximal portion, and upon movement of at least a portion of the adaptor in which this recess or indentation is defined, moves the control component. Exemplary control components of the handle may include a slider (which generates, for example, deflection of a tool tip upon movement) and/or a knob (which generates, for example, roll of the tool about the tool axis when rotated).

In some embodiments, the second geometry is shaped to match an outer contour of the proximal portion, for example, an outer contour of at least a part of a grippable handle. For example, the second geometry includes a main recess in which a body of a proximal handle is received, and at least one extension of the recess where a handle component which is integral with the handle body may be received, for example, a slider, a lock, a rotatable knob, and the like.

In some embodiments, the main recess is defined by inner walls of the adaptor housing, which are shaped and located to support at least a portion of the proximal portion received in the recess. In some embodiments, the recess is sized to fittingly engage the proximal portion, optionally being shaped and/or sized according to a proximal portion of a specific tool being engaged.

In some embodiments, inner walls of the adaptor housing which define the recess are located to counteract force applied onto the proximal portion by the movers of the adaptor. For example, walls at the recess restrict axial movement of a body of a handle when the slider of the handle is being compressed and pushed by a mover of the adaptor. In some embodiments, the recess is shaped and sized to provide for rotation of the proximal portion about the long axis, yet prevent axial movement and/or lateral (sideways) movement of the proximal portion within the recess. In some embodiments, the recess is shaped to allow only a predefined number of handle positions and/or a predefined extent of movement of handle control components, and restrict other movement. In some embodiments, movers of the adaptor are restricted in their extent of movement, optionally by the adaptor housing. For example, restricted in an axial sliding extent, restricted in a degree of rotation.

In some embodiments, at least a portion of the adaptor housing is configured to slide linearly with respect to a body of the proximal portion received within the recess. Optionally, movement of a portion of the housing moves a proximal portion control component relative to body of the proximal portion, for example, pushes or retracts a slider of a handle relative to the handle body.

In some embodiments, the first geometry and the second geometry are co-axial. In some embodiments, the first geometry is located radially outwardly relative to the second (inner) geometry. In some embodiments, one or more walls of the outer geometry extend to at least partially encase the inner geometry or vice versa, so that movement of one of the geometries causes respective movement of the second geometry.

In some embodiments, control components at a proximal portion of the tool which are engaged by the adaptor are moved relative to a body of the proximal portion by generating relative movement between the first and second geometries. In some embodiments, movement comprises rotation (e.g. rotation of the second geometry while the first geometry is stationary; rotation of the first geometry while the second geometry is stationary; rotation of both geometries). In some embodiments, movement comprises axial advancement and/or retraction of one or both the inner and outer geometries.

In some embodiments, the proximal portion (including the one or more integral components) is moved as a single unit by the adaptor, for example, rotated about the proximal portion long axis.

In an example, an elongate surgical tool proximal portion comprises a handle having a main body (for example, a cylindrical body) and a slider mounted onto the body and configured to move axially along at least a portion of the handle body (for example for generating deflection of a distal tip portion of the tool, e.g. of a guidewire). An adaptor for operably coupling this handle to one or more motors of a robotic device may be comprised of a housing in which at least a portion of the handle is received; an inner geometry which matches at least a portion of the external contour of the handle and fittingly surrounds the slider; and an outer geometry attached to a lead screw or a pin extending from the robotic device and driven (e.g. advanced or retracted) by one or more motors of the robotic device. In use, linear movement of the lead screw or pin carries the outer geometry linearly along. Since the outer geometry of the adaptor interfaces with the inner geometry of the adaptor (such as via an at least partial enclosure and/or an interference fit coupling), linear movement of the outer geometry causes movement of the inner geometry along, thereby sliding the slider with respect to the body of the handle, which remains stationary. In another usage example, the adaptor is rotated (either as a whole or only the inner geometry) to produce rotation of the handle as a whole, generating roll of the elongated tool about the elongated tool's long axis. In another example, a handle comprises a rotatable knob for fine roll adjustment of the elongated tool tip, and the knob is engaged by a mover of the adaptor (e.g. a gear wheel) which in turn rotates the knob.

An aspect of some embodiments relates to manipulation of a proximal portion of an elongate surgical tool via a robotic system. In some embodiments, the proximal portion is controlled by one or more controllers of the system. Optionally, the proximal portion is controlled remotely via a remote control device. In some embodiments, the robotic system is additionally configured for manipulation of a more distal portion of the tool extending from the proximal portion (e.g. for driving a less proximal portion of a guidewire located distally relative to the proximal portion) and optionally additional tools (e.g. a microcatheter, guiding catheter). In some embodiments, manipulation of the proximal portion of a tool (such as via the adaptor) is coordinated with other manipulations carried out by the robotic system on this tool, for example, axial advancement and/or retraction of the tool, roll of the tool. A potential advantage of controlling the proximal portion in coordination with manipulation of a more distal portion of the tool may include gaining or improving fine control over a distal most portion of the tool, for example, gaining or improving fine control of tool tip movement. A potential advantage of controlling the proximal portion in coordination with manipulation of a more distal portion of the tool may include additional support for executing such manipulations, such as, for example, by rotating both the proximal portion and the tool itself at a more distal location, instead of rotating only the tool and having the proximal portion passively rotate with it, or even interfere with the rotation manipulation.

An aspect of some embodiments relates to provision of a variety of adaptor configurations for engaging a respective variety of tool proximal portion configurations. In some embodiments, the variety of adaptor configurations are provided either in the form of a variety of single-unit adaptors, or as a variety of two-part adaptors, each having a different inner adaptor geometry, which interfaces with a same outer adaptor geometry (i.e. an outer adaptor geometry which is common to the variety of adaptor configurations). Whether provided as a single-unit adaptor, or as a two-part adaptor, each of the various configurations is configured to match the tool's proximal portion both in structure and in function.

In some embodiments, the adaptor comprises a plurality of movers each shaped and configured to engage a proximal portion component: for example, a mover configured as a slidable mounting which fits onto a slider; a mover configured as a rotating gear for rotating a knob located in the proximal portion. In some embodiments, a mover is integral with the recess for holding the proximal portion, and having a size and shape fitting with a control component of the proximal portion. For example, a mover is formed as an indentation extending radially outwardly from the recess in which the proximal portion is received. In an example, an indentation in a recess is shaped and sized to fit onto a slider of the handle. In some embodiments, the adaptor attaches the proximal portion, directly or indirectly (such as via mechanical transmission), to one or more motors of the robotic system which actuate movement of the movers and/or of the adaptor portions and/or of the adaptor as a whole. Additionally or alternatively, the adaptor comprises one or more integrated motors.

In some embodiments, manipulation of proximal portion components by the movers of the adaptor is set to match a type and/or extent and/or speed of movement which is specific to the design of the tool's proximal portion. Optionally, manipulation of a proximal portion component (e.g. a pushing of a slider, rotation of a knob) by a mover of the adaptor is performed in increments and/or to a degree selected to match the extent and/or direction and/or degree of movement of the proximal portion component.

In some embodiments, movement of proximal portion components is performed relative to a calibrated (home) position of these components, for example, a position of a proximal portion component relative to a body of the proximal portion to which it is movably attached (e.g. a slider position along a longitudinal extent of a handle body). Optionally, the calibrated position is specific to the proximal portion and the adaptor movers are pre-set accordingly. In some embodiments, pre-setting is by controlling one or more motors which actuate movers of the adaptor to position (optionally return) the movers to a position in which the proximal portion components are at their home position. Returning to the home position, in some embodiments, takes place automatically, such as upon turning the system on and/or off, upon engagement of the adaptor and the proximal portion, and/or other.

In some embodiments, a user (e.g. physician, technician) inputs into the system which proximal portion type is being used, and the activation parameters of the adaptor and/or its movers are set accordingly. Additionally or alternatively, the system recognizes the type (e.g. structure) of proximal portion being used (e.g. handle, torquer units), and activation parameters are set accordingly. The system may recognize the proximal portion presence (e.g. recognize connection to the adaptor) and/or identify the proximal portion type and/or shape using one or more sensors, such as proximity sensors, magnetic sensors, encoders or the like. In some embodiments, the system recognizes the proximal portion presence and/or type and/or shape using imaging means. In some embodiments, the system recognizes the proximal portion presence and/or type and/or shape using identification means, such as an RFID tag.

In some embodiments, the adaptor is structured to allow manual operation of the adaptor movers and/or to allow access to the proximal portion for direct manual manipulation of the proximal portion components.

In some embodiments, the adaptor comprises a removable cover through which a user may manually contact the movers of the adaptor and/or the proximal portion components directly. Optionally, if manual operation is performed, motor actuation of the adaptor movers is halted, for example by means of a clutch which disengages the motor from the mover and/or from one or more force transmission elements transferring force from the motor to the adaptor mover.

In some embodiments, the adaptor comprises a quick-eject mechanism for releasing the proximal portion, such as to provide for manual operation of the proximal portion.

While some examples are described herein with respect to a guidewire, it is noted that mechanisms and/or methods for example as described may be used with any elongate surgical tool, for example a microcatheter, a steerable catheter, a stent retriever, and/or any other elongate tool which movement and/or mechanical properties are affected by manipulation of a proximal portion of the tool, such as of a handle of the tool.

As referred to herein, a tool "proximal portion" or "handle" may include, for example, a tool portion configured for affecting and/or controlling movement and/or mechanical properties (e.g. stiffness) of a more distal tool portion, optionally, of a distal tip of the tool. For example, control components at a proximal portion of the tool (e.g. a slider, a knob) are configured to generate, when actuated, deflection of a distal tip of the tool, rotation (e.g. roll) of a distal tip of the tool.

In some embodiments, the proximal portion (in some embodiments, a handle) comprises a grippable or otherwise manually engageable portion. Optionally, the proximal portion is commonly manually operated (e.g. engaged by a user's hand and/or fingers). In some embodiments, the proximal portion is at a proximal-most end of the elongate surgical tool.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Exemplary Adaptor Coupling and Operation

Figure 1A:
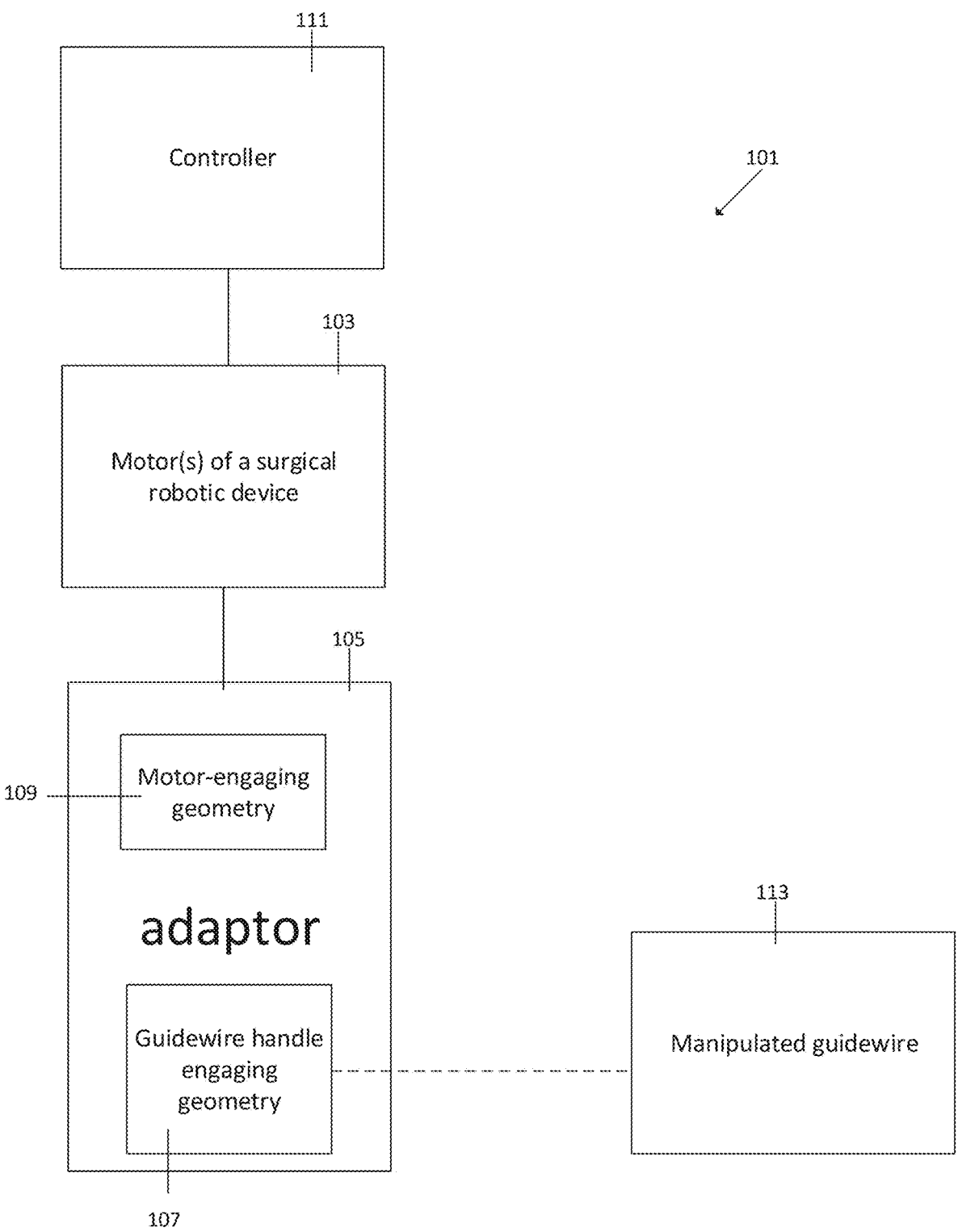
FIG. 1A is schematic diagram of a mechanism for coupling a handle of an elongate surgical tool to a surgical robotic device and manipulating the handle via the robotic device for affecting a distal portion of the elongate surgical tool, according to some embodiments.

Referring now to the drawings, FIG. 1A is schematic diagram of a mechanism 101 for coupling an exemplary guidewire handle to a surgical robotic device and manipulating the handle via the robotic device, according to some embodiments.

In some embodiments, a guidewire handle is operably coupled to the robotic device, for example to one or more motors of the robotic device 103, via an adaptor 105.

In some embodiments, adaptor 105 is shaped and configured for engaging the guidewire handle so as to operably couple the handle to the one or more motors (and/or to motor transmission) of the robotic device. In some embodiments, the adaptor comprises a first motor-engaging geometry 109 shaped to attach to the one or more motors (or to motor transmission) of the robotic device, and a second handle-engaging geometry 107 shaped to attach to or to receive the guidewire handle therein.

In some embodiments, motor(s) 103 are controlled by a controller 111 of the surgical robotic device. In some embodiments, the controller is in communication with a user interface device (e.g. a remote control device), and is programmed to receive instructions from the user interface device and to actuate the motor(s) accordingly.

In some embodiments, in use, manipulation of one or more components of a guidewire handle engaged with the adaptor is performed by actuating the surgical device motor(s) or associated transmission. In some embodiments, the adaptor is shaped to operably contact one or more handle components such as: slider elements, rotatable knobs, push buttons, moveable locks. Upon actuation of the robotic device motor(s) by the controller, the motor engaging geometry moves and thereby generates movement of the handle engaging geometry, which in turn moves the components of the guidewire handle.

In some embodiments, movement of the handle components affects a more distal portion and/or a distal tip of the guidewire 113. For example, movement of handle components generates guidewire manipulations such as: roll of the guidewire (i.e. about the guidewire long axis); deflection of a distal portion of the guidewire; a change in the guidewire stiffness (e.g. by advancing or retracting a thread in a guidewire comprised of multiple threads, for example displacing a thread in a double-threaded guidewire), expansion of the tool diameter (for example by introducing fluids into the tool, optionally by injection), deployment of a structure originally enclosed inside the tool.

Figure 1B:
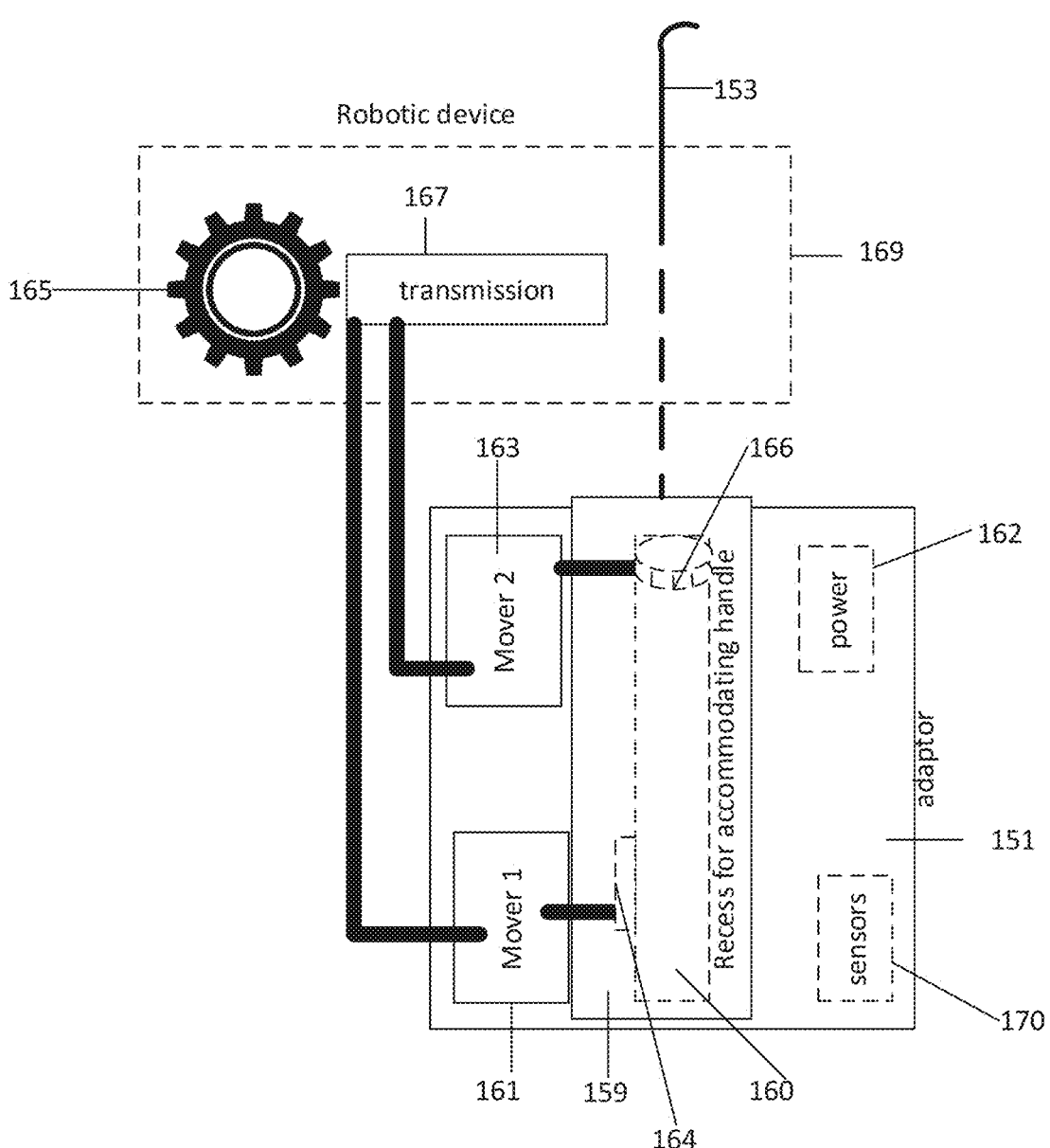
FIG. 1B is a schematic diagram of an adaptor which couples a handle of an elongate surgical tool to motorized actuation, according to some embodiments.

FIG. 1B is a schematic diagram of an adaptor which couples a guidewire handle to motorized actuation, according to some embodiments.

In some embodiments, an adaptor 151 is configured to couple a proximal portion (e.g. a handle 160) of a guidewire 153 to a surgical robotic device 169.

In some embodiments, adaptor 151 comprises a housing 150 which defines a recess 159 in which at least a portion of the guidewire handle is received. In some embodiments, the housing accommodates at least one mover such as movers 161, 163) positioned and configured to mechanically engage one or more control components of the guidewire handle received within the recess. In some embodiments, a mover is configured to rotate, slide, and/or otherwise move to cause respective movement of a handle component. In some embodiments, each mover is independently coupled to a transmission. Optionally, movers are activated independently of each other.

In the example shown, mover 161 is placed in contact with a slider 164 of the handle, so that it moves the slider when actuated; and mover 163 is placed in contact with a rotatable knob 166 of the handle, so that it rotates the knob when actuated.

In some embodiments, electrical and/or mechanical actuation of the mover(s) is by one or more motors 165 and/or via motor transmission 167 of the surgical robotic device 169.

In some embodiments, motor transmission elements include lead screws, rods, gears, and/or any other element suitable for mechanically transferring motor movement to the one or more movers of the adaptor.

In some embodiments, the inner walls of housing 150 at recess 159 are shaped to match a contour of handle 160. Optionally, the handle is fittingly received within the recess, for example such that lateral movement of the handle inside the recess is prevented. In some embodiments, the handle is allowed to rotate about its axis inside the recess.

In some embodiments, the inner walls of the housing support the handle, for example the body of the handle, from at least two faces. In some embodiments, the handle is received within the recess such that the inner walls of the housing counteract force applied onto the handle, for example force applied by movers 161, 163. In an example, mover 161 is compressed onto slider 164 in order to move the slider axially, while a body of the handle remains held and supported by the walls of the housing at the recess, so that the handle body does not move, and only the slider does move. In some embodiments, adaptor 151 comprises one or more sensors 170, configured to measure or otherwise indicate, for example: whether a handle had been received inside the recess; a position of the mover(s) relative to the handle; a position of handle components (e.g. an axial position of the slider, a rotational angle of the knob). In some embodiments, a relative position of a mover is indicated by sensing a position of the motors and/or of the motor transmission, which actuates the mover (for example, via a counter that counts motor rotations). In some embodiments, a position of a mover and/or of a handle component is sensed using an encoder, e.g. an optical encoder. In an example, the encoder is configured along an axial path along which the mover that pushes the handle slider moves, and is configured to measure the extent of axial movement and optionally communicate that distance extent to a system controller. In some embodiments, one or more sensors are integrated and/or mounted on a transmission of the mover, for example, on a pin or rod coupling the mover to a device motor.

In some embodiments, adaptor 151 includes integrated powering means 162, e.g. a battery. Optionally, the powering means supply power to the movers and/or to one or more sensors of the adaptor. In an example, a battery is activated only upon use of the adaptor. In a specific example, a zinc-air type battery is activated when exposed to air, for example, insertion of a handle into the recess may move a slip which covers the battery, exposing the battery to activate it.

In some embodiments, at least a portion of guidewire 153 is operably received within the robotic device 169. In some embodiments, a most proximal portion (e.g. a handle) of the guidewire is received within adaptor 151; an intermediate portion of the guidewire is received within the robotic device 169; and a distal portion of the guidewire extends to be inserted into the patient body.

In some embodiments, robotic device 169 is configured to manipulate the guidewire, for example, to roll the guidewire and/or move the guidewire axially (i.e. advance and/or retract) the guidewire.

In some embodiments, robotic device 169 includes tool moving elements, such as wheels, which engage the guidewire at a location distal to the handle, to actuate the guidewire movement.

In some embodiments, robotic device 169 is configured to receive and actuate movement of a plurality of elongate surgical tools, for example, a guidewire, a microcatheter, a guiding catheter.

In some embodiments, manipulation of the guidewire via the guidewire handle, for example as described herein, is coordinated (e.g. synchronized) with movement of the guidewire which is carried out by the robotic device. For example, if roll of the guidewire is actuated via the guidewire handle, the tool moving elements of the robotic device may be actuated to generate similar roll of a more distal portion of the guidewire, potentially preventing twisting of the guidewire. In another example, deflection of a guidewire distal tip via the handle may be performed simultaneously to axial advancement and/or retraction of the guidewire and/or roll of the guidewire by the robotic device. In another example, a stiffness of the guidewire (e.g. of a double-thread guidewire) may be changed during axial movement and/or roll of the guidewire (e.g. by pulling one of the inner threads of the guidewire back).

In some embodiments, manipulation of the guidewire handle is performed taking into account an arrangement of more distal portions of the guidewire which are held or received within the robotic device. For example, a guidewire held by the robotic device may be turned (e.g. in U-shape curvature) one or more times. Optionally, when a guidewire is held by the robotic device at two positions, for example at the handle and at a more distal position along the guidewire length, a length of the guidewire between these two positions can be selectively modified in accordance with the advancement or retraction of the guidewire distal portion inside the patient. In some embodiments, the housing of the robotic device allows the guidewire to extend outside of the housing between these two positions, as to allow the in-between segment to increase or decrease in length without being limited by the confinements of the housing.

Figure 2:
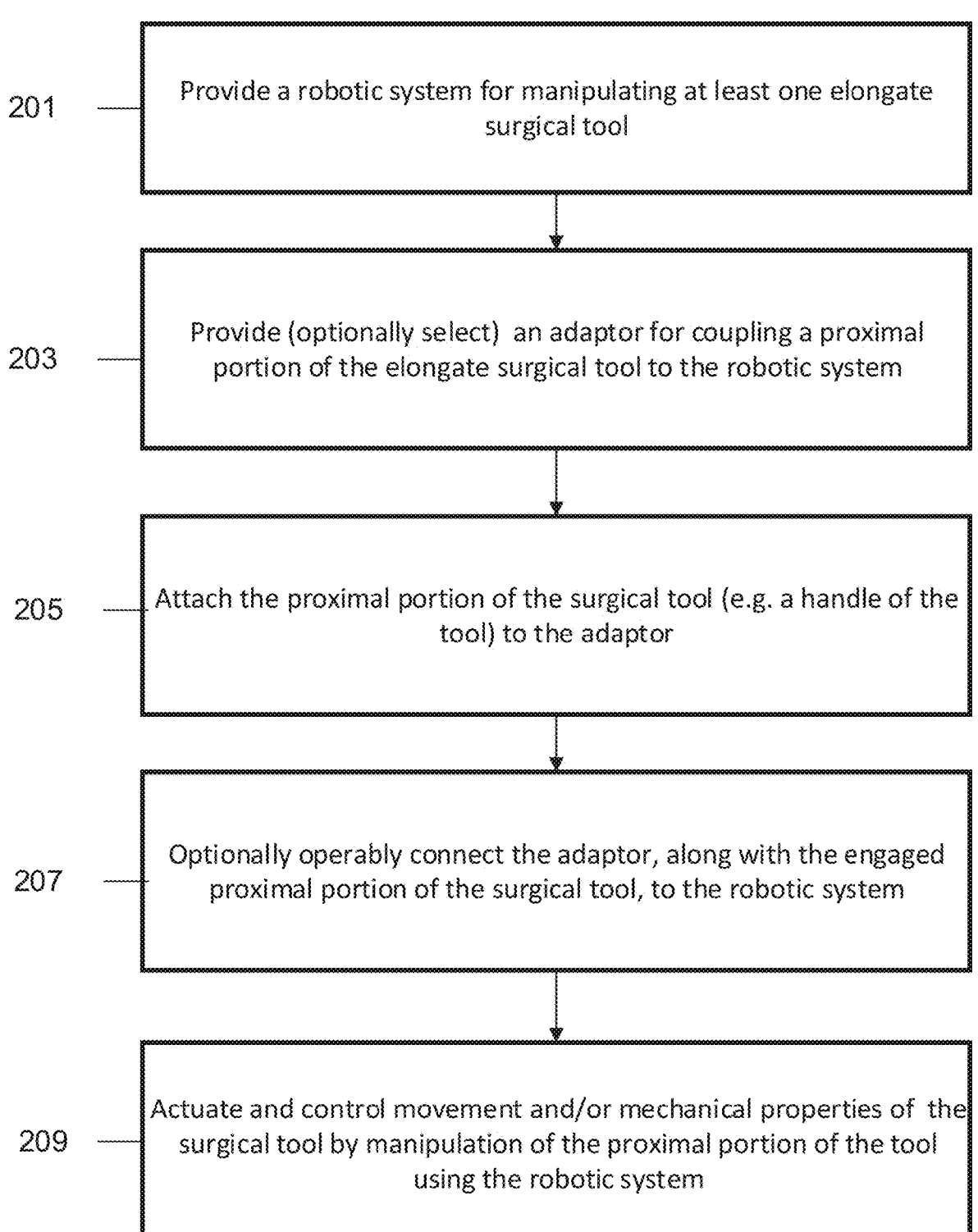
FIG. 2 is a flowchart of a general method for operably coupling a handle of an elongate surgical tool to a surgical robotic device, according to some embodiments.

Manipulation of tools such as a guidewire by the robotic device is for example as described in U.S. provisional application 62/941,842 and/or in U.S. provisional application 63/082,508 which are incorporated herein by reference. Exemplary Method for Operably Coupling a Tool Handle to a Robotic System FIG. 2 is a flowchart of a general method for operably coupling, for example, a guidewire handle to a surgical robotic device, according to some embodiments.

In some embodiments, a robotic system for manipulating at least one elongate surgical tool is provided (201).

In some embodiments, an adaptor for coupling a proximal portion of an elongate surgical tool to the surgical system is provided (203). Optionally, the adaptor is selected from among a plurality of adaptors having different shapes and/or sizes. In some embodiments, the adaptor is selected according to a geometry and/or function of the tool proximal portion. For example, for a tool handle comprising a rotatable knob, an adaptor including a mover suitable for rotating the knob is selected. For example, for a guidewire handle comprising a slider, an adaptor including a mover suitable for advancing and/or retracting the slider is selected. In some embodiments, at least a portion of the adaptor (e.g. only the motor-engaging portion of the adaptor, or the entire adaptor) is provided as part of the robotic system in 201.

In some embodiments, the adaptor is designed to engage a handle having a specific design. Optionally, different adaptors are designed to engage handles of different shapes and/or designs, such as handles of tools by different manufacturers. Since different handles may have different "neutral" (or calibration) positions of the tool, in some embodiments, the adaptor is designed to match the neutral position dictated by the handle, for example so that manipulation of the handle may be carried out relative to the particular neutral position. In some embodiments, the adaptor includes a portion which is shaped to match an outer contour of the handle.

Additionally or alternatively, an adaptor may include at least one adjustable portion which may be moved, enlarged, reduced and/or otherwise modified to engage more than one handle type or configuration.

In some embodiments, a proximal portion of the tool (e.g. a handle) is attached to the adaptor (205). Optionally, attachment is performed by a user (e.g. a physician, nurse, and/or other clinical personnel). In some embodiments, attachment includes inserting at least a portion of the handle into a designated recess of the adaptor. Additionally or alternatively, the adaptor is "dressed" or fitted onto the handle.

In some embodiments, the adaptor along with the tool handle engaged by it are connected to the robotic system (207). Alternatively, in some embodiments, the adaptor is constructed as an integral part of the robotic system, and does not require separate attachment to the system. Alternatively, in some embodiments, the adaptor is pre-assembled onto a guidewire (e.g. to a guidewire handle) and is provided along with the guidewire. Optionally, the user then connects the assembly of the adaptor and guidewire to the system. In some embodiments, the adaptor and the guidewire are provided preloaded with the robotic system.

In some embodiments, connecting the adaptor to the robotic system establishes a mechanical coupling of the adaptor to motor(s) and/or to motor transmission of the robotic system. In some embodiments, connecting the adaptor to the robotic system establishes an electrical coupling of the adaptor to the robotic system, for example to electrical powering of the system.

In some embodiments, the proximal portion of tool (e.g. a guidewire handle) is then manipulated, via the robotic system, to affect movement and/or mechanical properties of the tool (209). In some embodiments, a user controlling the robotic system (such as via a user interface, optionally configured as a remote control device) manipulates the proximal handle of the tool.

In an example, the user instructs (e.g. via a remote control device) to deflect a distal tip of the tool (e.g. a guidewire). Then, one or more motor(s) of the robotic system actuate movement of mover(s) in the adaptor, which in turn contact a handle component, for example, a slider, moving the slider to deflect the distal tip of the tool. In another example, the user instructs (e.g. via the remote control device) to roll the tool (e.g. a guidewire, or a steerable catheter). Then, one or more motor(s) of the robotic system actuate movement of mover(s) in the adaptor, which in turn contact a handle component, for example, a rotating knob, turning the knob to roll the tool (such as roll a guidewire about the guidewire long axis). In another example, the user instructs (e.g. via the remote control device) to change mechanical properties of the tool, such as stiffness of a distal portion of the tool. Then, one or more motor(s) of the robotic system actuate movement of mover(s) in the adaptor, which in turn contact a handle component, for example a puller/pusher configured to advance or retract a thread of a double-threaded guidewire, thereby affecting the guidewire stiffness. Examples of double threaded guidewire include a guidewire having an inner thread disposed within a lumen of an outer thread; or a guidewire including two threads lying adjacent each other or passing through the outline of a main thread. In some embodiments, deflection of a distal portion of the guidewire is achieved by moving a thread (e.g. advancing or retracting).

In some embodiments, an extent and/or speed of moving handle components (e.g. a degree of rotation of a knob; a distance in which a liner slider is moved) is set per the particular handle type engaged by the system. For example, motorized movement of a slider by the robotic system is controlled to advance and/or retract the slider within a distance range determined for the particular handle. For example, motorized movement of a rotating knob by the robotic system is controlled to rotate the knob at a speed and/or degree of rotation suitable for the specific knob. In some embodiments, an adaptor configured to engage a certain handle type includes and/or is pre-set with motor actuation parameters for driving the adaptor movers in a manner that matches the specific movement of the handle components. Motor actuation parameters are set, for example, to control a speed of movement, a direction of movement, a degree or extent of movement.

Exemplary Robotic System

Figure 3:
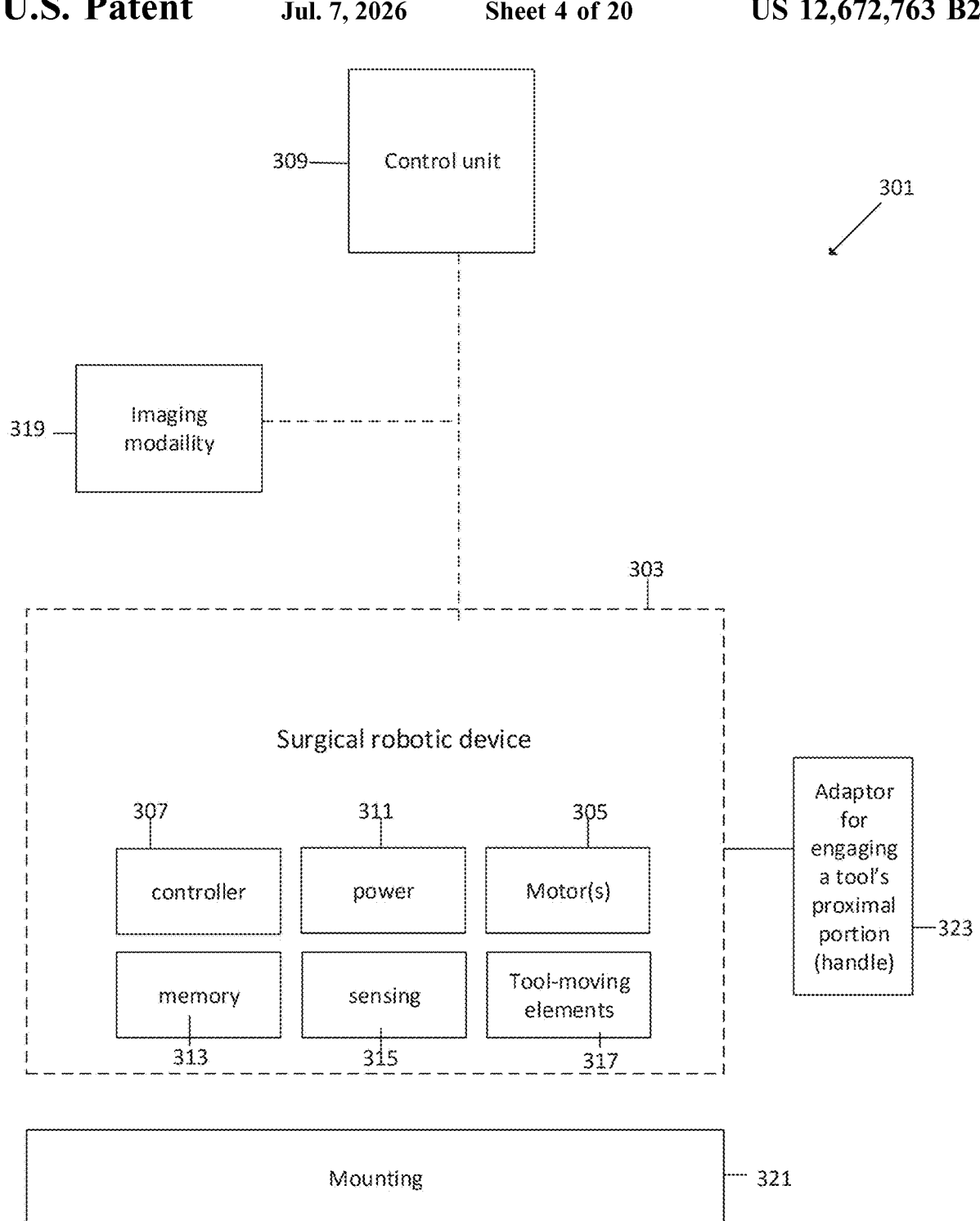
FIG. 3 is a block diagram of a surgical robotic system configured for engaging and controlling a proximal portion (e.g. a handle) of a an elongate surgical tool, according to some embodiments.

FIG. 3 is a block diagram of a surgical robotic system configured for engaging and controlling a proximal portion (e.g. a handle) of, for example, a guidewire, according to some embodiments.

In some embodiments, a robotic system 301 is suitable for use in a surgical room. Optionally, one or more system components (such as controlling components, imaging components) are physically separate from the rest of the system and may be used remotely.

In some embodiments, system 301 is configured to receive one or more surgical tools (e.g. a guidewire, a microcatheter, a guiding catheter, an intermediate catheter, and/or other elongate and/or endoluminal surgical tool) and to actuate movement of the tools.

In some embodiments, the system is configured to drive linear movement (e.g. advancement and/or retraction) of a tool received therein, and/or drive rotational movement (e.g. axial rotation) of a tool received therein. In some embodiments, linear and rotational movements are actuated simultaneously.

In some embodiments, system 301 includes a robotic device 303 which includes one or more of the following components:

one or more actuators such as one or more motors 305, and optionally associated transmission of the motors.

Tool moving elements 317, such as wheels, configured to operably contact a tool received by the system to move the tool (e.g. advance, retract, rotate the tool).

a controller 307, configured to receive and/or send operation signals to and/or from a general control unit 309. General control unit 309 may be configured as a remote control device, a console, a control unit physically attached to the system base, or a combination thereof. In some embodiments, the controller 307 is configured to coordinate manipulation (e.g. linear movement, rotation) of tools received and operated by the robotic system.

powering means 311, including for example a battery and/or connection means for mains electricity.

sensing means 315, for example, one or more sensors configured for detecting, for example, whether a tool has been inserted; a relative position of the tool; a position of tool-moving elements (e.g. wheels); actual movement of the tool-moving elements (e.g. by a counter counting the number of wheel rotations); sensors for communicating with other system sensors, and/or for other measurements and/or indications. In some embodiments, sensors are configured for detecting motor status, for example, a motor position, a motor rotation rate. Sensors of various types may be used, such as optical sensors, pressure sensors, force measurement sensors, speed sensors, sensor for detecting electrical current, flow sensors, position sensors (e.g. optical, magnetic, electrical position sensors).

a memory 313, which stores, for example, parameters related to tool movement, such as speed of movement, rotation, translation, angulation, deflection angle; indications obtained by one or more system sensors, such as a measure of force acting on the tool, stiffness of the tool; parameters related to the patient body and sensed by the inserted tools (e.g. heart rate, blood pressure, temperature, oxygenation level, and/or other sensed parameters).

In some embodiments, system 301 includes an integrated imaging modality 319. Alternatively, the system is configured to be operably attached to (for example, communicate with) an existing imaging modality. An imaging modality may include, for example, X-ray fluoroscopy, CT, cone beam CT, CT fluoroscopy, MRI, ultrasound, or any other suitable imaging modality.

In some embodiments, system 301 comprises a mounting 321 for placing device 303 relative to the patient and/or relative to the surgical bed. In some embodiments, the mounting comprises or is configured to attach to an adjustable fixture. Optionally, a height and/or angle and/or distance of the system relative to the patient (e.g. relative to the location of body entry) and/or relative to the bed are adjustable.

In some embodiments, system 301, optionally as part of device 303, comprises or is configured to engage an adaptor 323 for operably engaging a tool's proximal portion, for example, a handle.

In some embodiments, the adaptor defines a mechanical engagement between the one or more motors 305 and one or more components of the handle which move the tool. For example, the adaptor connects one or more motor(s) or associated transmission with a slider and/or knob component of the handle which deflects the tool tip upon sliding; with a knob component of the handle which rolls the tool when rotated; and/or with other handle components. Additionally or alternatively, the adaptor itself includes one or more integrated motors for driving movement of the handle components.

In some embodiments, upon attachment to the system, the adaptor can be actuated via the system controls, for example via a remote control device controlled by a user. Additionally or alternatively, the adaptor can be controlled directly, for example via manual engagement by a user. Additionally or alternatively, the handle can be removed from the adaptor, and optionally controlled manually.

In some embodiments, the adaptor comprises one or more sensors. Optionally, the sensors are configured for measuring and/or indicating one or more of: whether a tool handle had been engaged by the adaptor; a relative position of handle components such as a slider or rotating knob (for example, relative to their calibrated or neutral position); a relative position of portions of the adaptor, such as the inner and outer geometries; a speed of movement of adaptor portions and/or handle portions; a speed of movement (e.g. rotation speed) of the handle as a whole, such as by rotation of the adaptor as a whole and/or rotation of the inner geometry of the adaptor.

Exemplary Positioning of a Robotic System

FIGS. 4A-B are an isometric view and a side view of a robotic surgical system positioned with respect to a patient, according to some embodiments.

In some embodiments, a robotic system 401 is positioned with respect to a patient 403, optionally, with respect to a surgical body entry point in the patient. The entry point may be selected from, but not limited to, the patient's groin (i.e., the femoral artery), arm (i.e., the radial artery) or neck (i.e., the jugular vein).

In some embodiments, system 401 is mounted onto a rigid fixture 405. In some embodiments, the fixture is placed and/or restrained to the patient body: Additionally or alternatively, the fixture is attached to the surgical bed.

In some embodiments, fixture 405 is adjustable to control one or more positioning parameters of system 401, for example: a height, an angle (e.g. an angle of insertion into the body entry point), and a distance from the patient (e.g. from the entry point). Optionally, fixture 405 includes a rail on which system 401 can slide to be advanced towards and/or retracted from the patient.

In some embodiments, fixture 405 is manually adjustable, for example via a plurality of adjustable knobs 407.

A potential advantage of a relatively small and compact system may include that the system can be positioned relatively close the patient (e.g. to the body entry point), for example, at a distance of less than 2 cm, 3 cm, 5 cm, 10 cm or intermediate, longer or shorter distance from the entry point.

In some embodiments, system 401 is compact and occupies a relatively small volume (e.g. a volume of less than 2000 cm^3, 2500 cm^3, 3500 cm^3, 5000 cm^3, 9000 cm^3 or intermediate, larger or smaller volume), enabling placing of the system in proximity to the patient (such as in proximity to the surgical entry point in the body). Alternatively, the system is mounted on the patient directly, e.g. assembled on the patient's leg or arm, in accordance with the surgical entry point. In some embodiments, the system is small enough so as not to interfere with other surgical room equipment, such as imaging modalities used during operation. Optionally, the system has only minimal or no floor footprint and/or ceiling footprint.

In some embodiments, attachment of the system to the surgical bed and/or to the patient may be carried out using straps, bands, a rigid mounting, and/or other attachment means. In some embodiments, attachment to the bed is carried out using a stand which is stabilized relative to mattress and/or to the rail of the bed and/or to the floor. The system can then be mounted on the stand, for example attached via a snap fit mechanism, magnetic means, straps (e.g. Velcro), and/or other. In some embodiments, the stand is adjustable so as to enable use with patients of various sizes and/or different bed height and the like. In some embodiments, when setting a position of the system, one or more of a height, entry angle to the body, alignment of the system relative to the patient are selected. The system position may be defined with respect to the patient body or parts thereof (e.g. relative to the surgical entry point) and/or relative to the surgical bed and/or relative to other surgical room equipment, e.g. relative to imaging modules.

Exemplary General Adaptor Structure

FIGS. 5A-B are cross section views of an adaptor for coupling a guidewire proximal handle to a surgical robotic device, according to some embodiments. FIG. 5A is a cross section view along the short (width) axis of the adaptor; FIG. 5B is a cross section view along the long (length) axis of the adaptor.

In some embodiments, an adaptor 501 defines an inner geometry 503 shaped and configured for interfacing a proximal handle of a tool (e.g. a guidewire handle); and an outer geometry 505 shaped and configured for interfacing with the robotic device.

In some embodiments, the inner geometry 503 defines a main recess 507 in which the handle (i.e. a body of the handle, not shown) is received. Optionally, one or more lateral recesses such as recess 509 are provided to accommodate a handle of a specific structure. For example, recess 509 is shaped and sized for fittingly accommodating a slider of a guidewire handle. In this example, main recess 507 defines a circular cross section profile along its width (forming a cylindrical lumen, as shown in FIG. 5B), but other recess profiles are also to be contemplated, for example: a squared cross section profile, a rectangular profile, a triangular profile, an elliptical profile, an arbitrary profile and/or other profile shaped to match an outer profile of a tool handle engaged by the adaptor. In some embodiments, main recess 507 is shaped and/or sized to allow for axial sliding of the adaptor relative to the handle body received therein. Optionally, the main recess is sized so that a radial distance is provided between an outermost wall of the handle body and an innermost wall of the main recess, for example a distance of at least 0.1 mm, 1 mm, 5 mm, 10 mm, or intermediate, longer or shorter.

In some embodiments, the outer geometry 505 defines one or more features for coupling to the robotic device. For example, the outer geometry comprises a recess 511 in which a lead screw 513 (or a pin, and/or any other elongate element) protruding from the robotic device (such as from a housing of the robotic device) is received.

In some embodiments, the inner geometry is configured to move relative to the outer geometry, or vice versa. Alternatively, both geometries move together, as a single unit.

In some embodiments, movement comprises rotation (e.g. rotation of the inner geometry while the outer geometry is stationary; rotation of the outer geometry while the inner geometry is stationary; rotation of both geometries). In some embodiments, movement comprises axial advancement and/or retraction of one or both the inner and outer geometries.

In the example shown herein, only the inner geometry 503 is configured to rotate along with rotation of the handle, such as to cause roll of the guidewire, while the outer geometry 505 remains stationary. In some embodiments, a handle (not shown) is rotated (e.g. by a pin or a lead screw extending from the robotic device and rotating at least the inner geometry), rotating along with the slider that is a part of the handle. Since the slider is fittingly received within recess 509 of the inner geometry, rotation of the handle causes rotation of the inner geometry along with it, or vice versa. In some embodiments, the more distal rotation of the tool causes the handle to rotate within the adaptor, or together with the adaptor.

In some embodiments, the outer geometry 505 moves axially (for example by axial movement of a rod or pin received within recess 511). When the outer geometry moves axially, it carries the inner geometry axially along with it. In turn, the slider is advanced or retracted relative to a body of the handle which is received within the main recess 507.

In some embodiments, the inner geometry is at least partially encased within the outer geometry, for example as shown in FIG. 5B: side walls 517 of the outer geometry extend to overlie the inner geometry, at least in part. Additionally or alternatively, portions of the inner geometry extend to overlie portions of the outer geometry. Additionally or alternatively, an interference fit coupling (e.g. respective protrusions and recesses) couple between the two geometries. In some embodiments, a coupling between the two geometries is configured to provide one or more of: that rotation of the inner geometry will simultaneously rotate the outer geometry; that rotation of the outer geometry will simultaneously rotate the inner geometry; that axial movement of the outer geometry will simultaneously move the inner geometry axially along.

In some embodiments, a handle is inserted into an adaptor by sliding (e.g. threading) the handle body into the main recess of the adaptor. Optionally, the handle is manually placed within a recess of the adaptor. Additionally or alternatively, the adaptor includes moving parts and/or separable parts (e.g. independent parts which can connect to each other) and is configured to be fitted over or on the handle. Additionally or alternatively, the adaptor comprises a cover (e.g. a lid) which can be moved to allow insertion of the tool handle into its designated recess.

FIGS. 6A-B are cross section views of an adaptor for coupling, for example, a guidewire proximal handle to a surgical robotic device, according to some embodiments.

In this example, the entire adaptor 601 (including both the inner geometry 603 and the outer geometry 605) is configured to rotate with the guidewire handle received inside it, when the adaptor is rotated.

In the adaptor structure shown, the outer geometry 605 is attached via a pin 607 to the robotic device. A circumferential slot 609 is defined along the outer geometry to accommodate the pin 607 regardless of a current rotational orientation of the adaptor. In use, this coupling ensures that the pin maintains attachment of the adaptor to the robotic device in all rotational positions of the adaptor.

FIGS. 7A-C schematically show examples of alternative configurations of adaptors in which a guidewire handle is received, for coupling the handle to a surgical robotic device, according to some embodiments.

In FIG. 7A, an adaptor housing 701 rotates along with a handle 703 that is held inside it, in accordance with some embodiments. A slider 705 of the handle is accommodated within a designated recess 707 in the adaptor housing. In some embodiments, a mover 709 of the adaptor is configured to axially move the adaptor housing relative to the handle, generating axial movement of the slider relative to the handle. (i.e. relative to a body of the handle 706).

In FIG. 7B, only the handle 703 is rotated while the adaptor housing 711 remains stationary. Slider 705 of the handle is allowed to rotate along with the handle within a designated circumferential slot 713.

In FIG. 7C, an adaptor 715 includes an integrated motor 717. In use, the motor drives axial translation of a mover 719 which in turn moves slider 705 axially. As further shown, the adaptor 715 rotates (along with the motor 717 and the mover 719) to rotate the handle 703 as a whole (i.e. including the body of the handle and the slider).

Commonly, the slider would rotate along with the handle body when the handle body is rotated. In some embodiments, the rotating slider would push on the walls of the inner geometry of the adaptor and cause the inner geometry to rotate along with the handle. Alternatively, the inner geometry would push on the slider walls, causing the handle to rotate with it.

In some embodiments, rotation of the inner geometry would further lead to rotation of the outer geometry (for example due to an interference coupling and/or an encasing of the inner geometry within the outer geometry, or vice versa), and both geometries would rotate together.

FIGS. 8A-F schematically show various positions of a guidewire handle within an adaptor for example as described in FIG. 7B, and a corresponding resulting effect on a distal end portion of the guidewire, according to some embodiments.

The adaptor shown in these figures is for example as described in FIG. 7B.

Figure 8A:
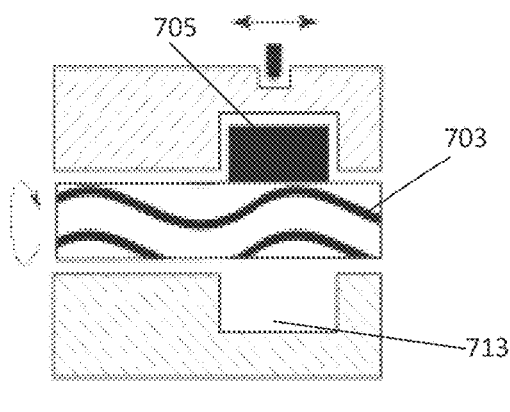
Figure 8B:
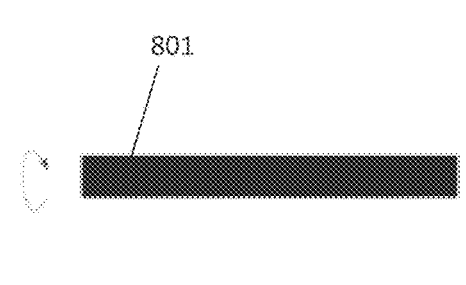

In FIG. 8A, handle 703 is rotated while slider 705 is allowed to rotate within the designated circumferential slot 713. Rotation of handle generates roll of a more distal portion 801 of the guidewire (or of the guidewire as a whole), as shown in FIG. 8B.

Figure 8C:
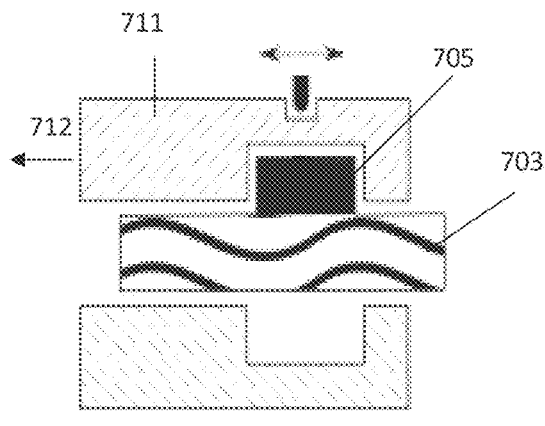
Figure 8D:
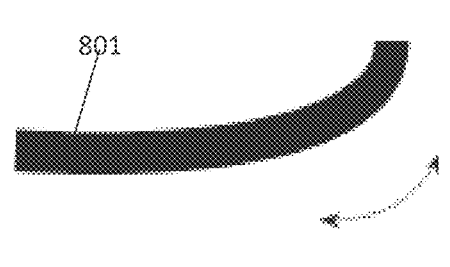

In FIG. 8C, adaptor housing 711 is moved (e.g. pushed) in a proximal direction (see arrow 712) relative to the handle 703, pushing slider 705 proximally. Axial movement of the slider generates deflection of a more distal portion 801 of the guidewire, for example, deflection of the distal tip of the guidewire, as shown in FIG. 8D. In some embodiments, when adaptor housing is moved in the opposite direction (distally), the slider is pushed distally, causing deflection of the guidewire tip to the opposite side.

Figure 8E:
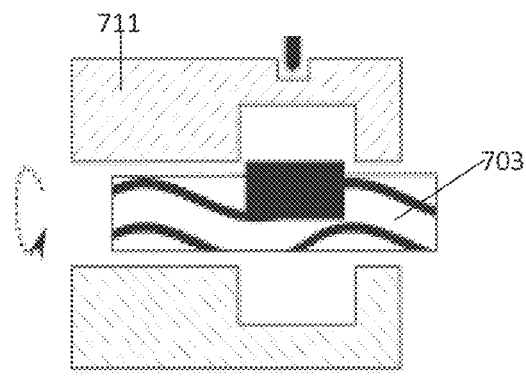
Figure 8F:
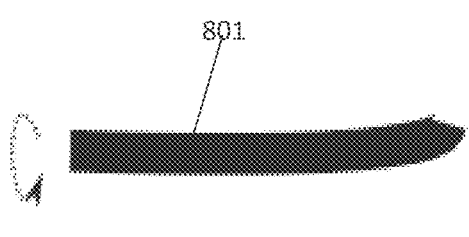

In FIG. 8E, rotation of handle 703 after pushing of the adaptor housing 711 proximally (which pushes slider 705 proximally) generate roll of the guidewire while the guidewire tip is deflected, as shown in FIG. 8F.

Figure 9A:
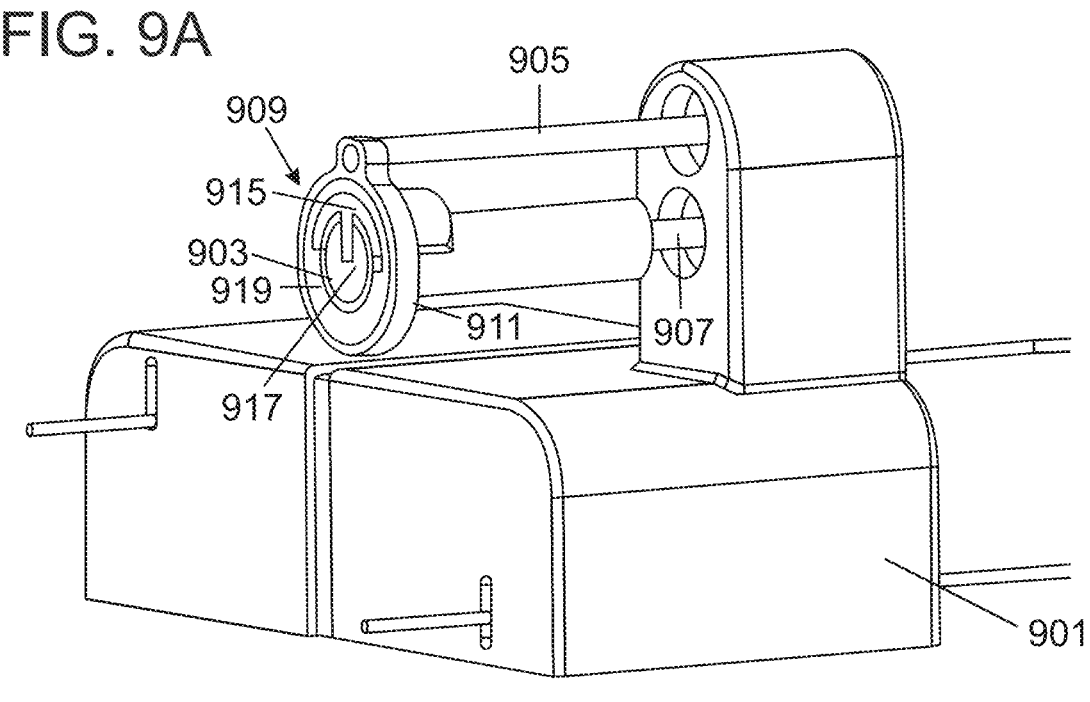
Figure 9B:
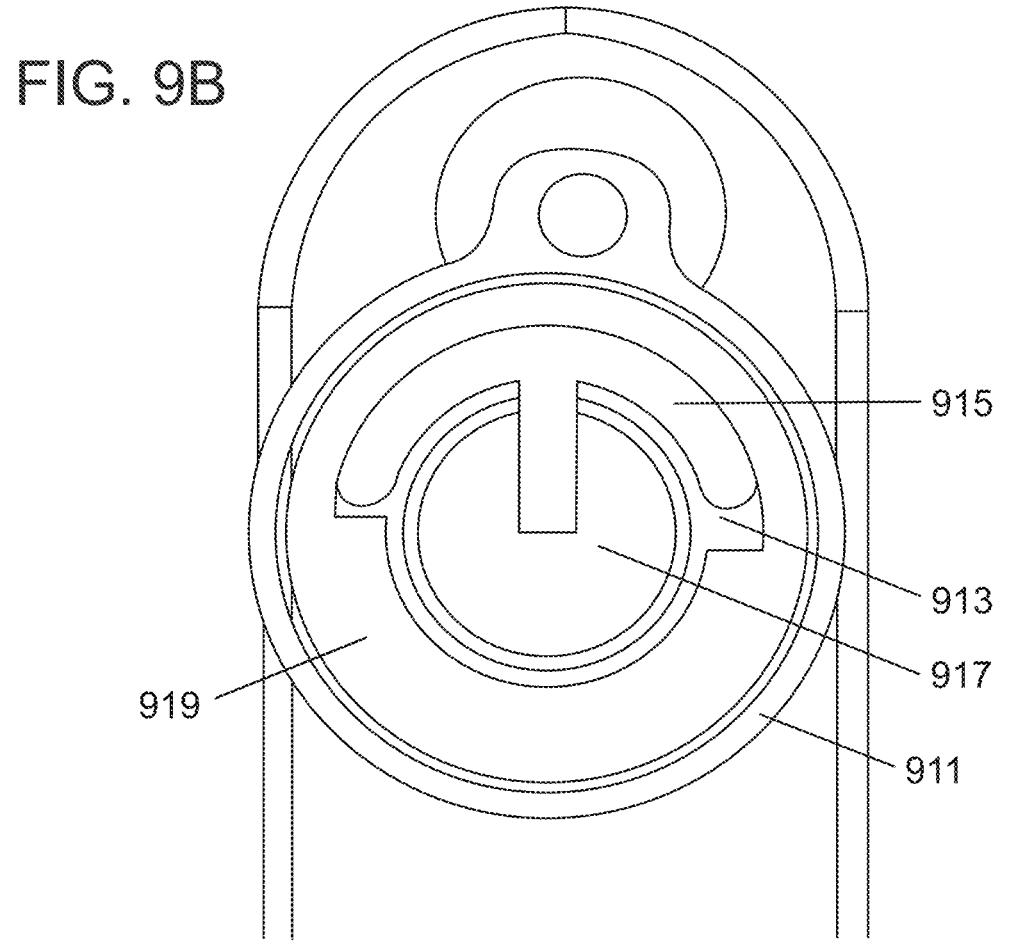

FIGS. 9A-B are an isometric view (FIG. 9A) and a cross section view (FIG. 9B) of an exemplary mechanism for engaging a proximal handle of a guidewire, according to some embodiments.

In some embodiments, the robotic device 901 is configured to operably engage a proximal handle 903 of a tool, for example, of a guidewire manipulated by the robotic device.

In some embodiments, one or more extensions of the device such as a lead crew 905 or a pin 907 protrude outwardly to engage the tool handle, optionally via an adaptor 909. In the example shown, lead screw 905 is received within a recess 910 defined in the outer geometry 911 of the adaptor. In some embodiments, as shown, the inner geometry defines a recess 913 in which a slider 915 of the handle is fittingly received. In use, lead screw 905 is configured to move axially towards and/or away from the device (optionally, the screw is rotated to cause its advancement/retraction), pulling the outer geometry 911 along with it. Moving the outer geometry 911 axially would in turn carry the inner geometry along, thereby moving the slider 915 axially relative to a main body 917 of handle 903.

In some embodiments, pin 907 is coupled to the handle body 917 to rotate the handle body. In some embodiments, pin 907 is an integral portion of the handle. In such embodiment, the pin may be coupled to a motor which drives its rotation by a mechanical attachment, such as a snap-fit, press-fit, interference fit and the like. Alternatively, pin 907 is an integral part of the adaptor. Alternatively, pin 907 is an integral part of the robotic device. In use, rotation of the pin rotates the handle body and the attached slider along, and the slider causes rotation of an inner geometry 919 of the adaptor.

In some embodiments, movement of lead screws and/or pins and/or other elements for transferring axial and/or rotational movement to the adaptor and/or directly to the handle is actuated by one or more motors (not shown) housed within the robotic device 901.

Figure 9C:
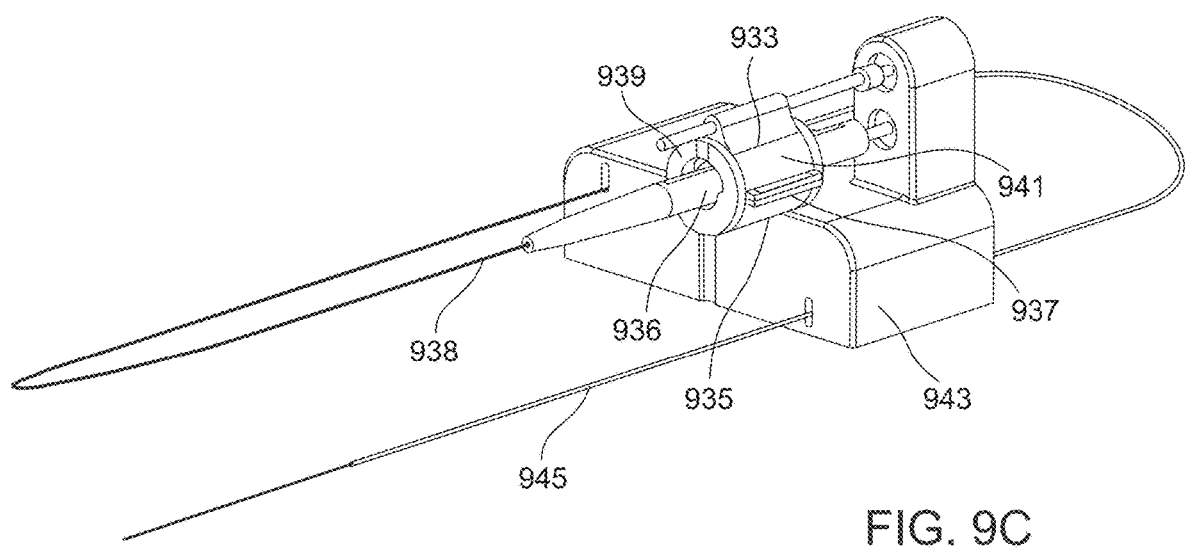
Figure 9D:
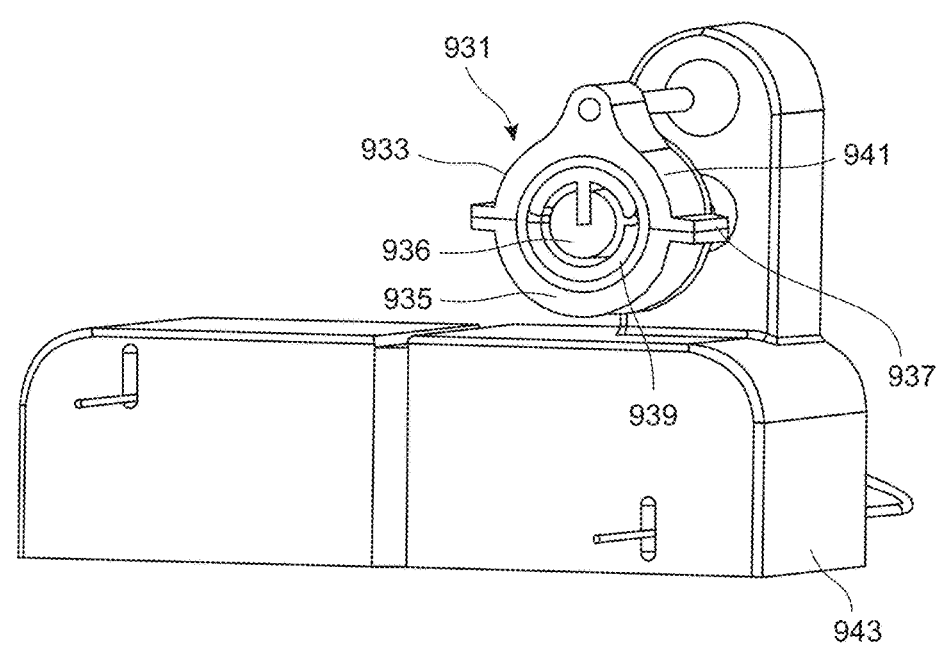

FIGS. 9C-D are an isometric view (FIG. 9C) and a cross section view (FIG. 9D) of another exemplary mechanism for engaging a proximal handle of a guidewire, according to some embodiments.

In this exemplary configuration, the adaptor outer geometry 931 is comprised of separable parts 933, 935 which can be fitted onto the adaptor inner geometry 939, and subsequently tool handle 936, and then connected to each other, for example via snap connections 937.

As further shown in this example, in some embodiments, portions of the inner geometry 939 of the adaptor (e.g. proximal and distal faces of the inner geometry, as shown) extend to at least partially overlie or encase portions of the outer geometry 941, for example as shown in FIG. 9C.

As further shown in this example, in some embodiments, a guidewire 938 extending from handle 936 is received by the robotic device 943. Optionally, at least a portion of the guidewire is inserted into a lumen of a microcatheter 945 which also extends through the robotic device to be manipulated by it.

Exemplary Adaptor Structures for Different Types of Tool Handles

In the following description of FIGS. 10A-12E, reference numbers are marked for the described components in the figure where the component is best seen.

FIGS. 10A-10E show a first example of a mechanism for engaging and actuating motorized movement of a guidewire handle for example as shown FIG. 10A, according to some embodiments.

FIG. 10A shows a tool handle (e.g. guidewire handle) 1001 having a substantially rectangular (e.g. box shaped) body 1003; a slider 1005 which moves linearly along at least a portion of the length of the handle body (such as to deflect a distal tip of the guidewire 1009; and a vertically oriented rotatable knob 1010 which is rotated (such as to generate fine roll adjustment of a tip portion of guidewire 1009).

In some embodiments, to operably couple the handle to a robotic device, an adaptor 1011 is provided. In some embodiments, the adaptor includes an external housing 1013 and a plurality of movers configured to engage the handle components, such as the slider and the rotating knob, to move them. In some embodiments, the movers include a slider-engaging mover 1015 which fits directly over the slider 1005 and upon movement, is configured to move (e.g advance or retract) the slider along with it. In some embodiments, the movers include a knob-engaging gear 1017 which is positioned and configured, when rotated, to rotate knob 1010.

In some embodiments, movement of the slider-engaging mover 1015 is actuated by a motor 1019. In some embodiments, rotation of the knob-engaging gear 1017 is actuated by a motor gear 1021. In some embodiments, rotation of the adaptor as a whole, to generate roll of the guidewire by rotating the handle as a single piece, is actuated by a gear 1023 driven by motor 1025. Optionally, gear 1023 is coupled externally to the adaptor housing 1013.

In some embodiments, a mover such as 1015 is configured for direct manual engagement by a user. Manual engagement may be performed, for example, in case of device failure, medical emergency and/or when a specific manual manipulation is desired (e.g. for fine tuning the tool tip). Optionally, the mover in the adaptor is coupled to a clutch mechanism which upon manual actuation releases the mover from its associated transmission. In the example shown, a push button 1020 on mover 1015, upon being pushed, disengages mover 1015 from its transmission (sliding pin 1022), for example by releasing a set of clasping legs 1024 which couple mover 1015 to pin 1022. Once mover is decoupled from its transmission, it can be manually moved (e.g. slid) to move the handle slider 1005.

FIGS. 11A-E show a second example of a mechanism for engaging and actuating motorized movement of guidewire handle as shown in FIG. 11A, according to some embodiments.

FIG. 11A shows a tool handle (e.g. guidewire handle) 1101 having a body 1103; a horizontally oriented rotatable knob 1110 which is rotated (such as to generate deflection of a tip portion of guidewire 1109); and a lock 1105 which locks the guidewire tip in a desired deflected position, for example by interfering with rotation of knob 1110.

In some embodiments, to operably couple the handle to a robotic device, an adaptor 1111 is provided. In some embodiments, the adaptor includes an external housing 1113 and a plurality of movers configured to engage the handle components, such as the lock and the rotating knob. In some embodiments, the movers include a lock-engaging mover 1115 which fits directly over the lock, and upon movement, is configured to move (e.g advance or retract, push downwards) the lock 1105.

In some embodiments, the movers include a knob-engaging gear 1117 which is positioned and configured, when rotated, to rotate knob 1110.

In some embodiments, movement of the lock-engaging mover 1115 is actuated by a motor 1119. In some embodiments, rotation of the knob-engaging gear 1117 is actuated by a motor gear 1121.

In some embodiments, rotation of the adaptor as a whole, to generate roll of the guidewire by rotating the handle as a single piece, is actuated by a gear 1123 driven by motor 1125. Optionally, gear 1123 is coupled externally to the adaptor housing 1113.

FIGS. 12A-E show a third example of a mechanism for engaging and actuating motorized movement of a proximal portion of a guidewire as shown in FIG. 12A (which does not have a proximal handle), according to some embodiments.

FIG. 12A shows a proximal portion of a guidewire which includes two graspers 1201, 1203. In some embodiments, each grasper holds a proximal end portion of a thread constructing a double-thread guidewire 1204. For example, grasper 1201 holds a first thread, and grasper 1203 holds a second thread. In use, translation of the graspers relative to each other generates pulls one thread relative to the other, producing deflection at a distal portion of the guidewire.

In some embodiments, to operably couple the double-thread guidewire to a robotic device, an adaptor 1205 is provided. In this example, the adaptor includes a mover 1207 which overlies at least grasper 1201 and is configured to move (e.g. axially slide) grasper 1201 relative to grasper 1203, such as to generate deflection of a distal tip of the guidewire. Optionally, movement of mover 1207 is driven by a motor 1209.

In some embodiments, rotation of the adaptor as a whole, to generate roll of the guidewire by rotating the handle as a single piece, is actuated by a gear 1223 driven by motor 1225. Optionally, gear 1223 is coupled externally to the adaptor housing 1213.

FIGS. 13A-B show a housing of an adaptor for engaging and actuating motorized movement of a guidewire handle, according to some embodiments.

In some embodiments, the adaptor constitutes a stand-alone unit, which may be mounted onto and/or placed adjacent the robotic device. In some embodiments, the adaptor itself houses one or more motor(s) and/or controller(s) for carrying out manipulation of the tool handle via the one or more movers of the adaptor. Additionally or alternatively, the adaptor is mechanically and/or electrically connected to the robotic system and actuation of one or more movers of the adaptor is by one or more motor(s) of the robotic device.

In the examples shown, an adaptor housing 1301 includes one or more electrical connectors, such as connectors 1303, 1305. Optionally, the electrical connectors are positioned and located according to a position of a corresponding electrical connection of the robotic device (not shown).

In some embodiments, the adaptor housing defines one or more mechanical connectors. For example, as shown, attachment legs 1307 extend from the housing to be mounted onto and/or received within a housing of the robotic device.

In some embodiments, the adaptor housing includes a conduit or opening 1309 through which the tool (e.g. guidewire) extending from the handle passes.

In some embodiments, dimensions of the adaptor housing are determined according a size of the handle engaged by the adaptor. For example, a length 1311 of the housing may range, for example, between 2 cm-20 cm; a width 1313 of the housing may range, for example, between 0.5 cm-10 cm; a height (thickness) 1315 of the housing may range, for example, between 0.5 cm-10 cm. The exemplary dimensions listed may be suitable for an adaptor which accommodates a handle that is approximately 1.5-20 cm in length, 0.4 cm-10 cm in width, 0.4 cm-10 cm in height.

FIG. 14 schematically illustrates a module 1400 of the surgical robotic device configured to operably engage an adaptor for coupling a proximal handle of a guidewire, according to some embodiments.

In some embodiments, the robotic device includes mechanical and/or electrical couplings for connecting to the adaptor. For example, one or more protrusions such as at least a portion of gear wheel 1401 and/or knob 1403 extend outwardly relative to a housing 1407 of the robotic device to engage the adaptor. In some embodiments, electrical connections 1405 are provided to electrically connect the adaptor to the robotic device.

FIG. 15 schematically illustrates motor engagement of a proximal portion of a "double thread" guidewire 1501, according to some embodiments.

In some embodiments, multiple threads (see 1503, 1505) of a guidewire (e.g. 2, 3, 4, 6 threads or intermediate, higher or lower number) can be engaged at their proximal ends to motor(s) and/or to motor transmission and/or to mover(s), such as gear wheels 1507, which are actuated by motors. In use, rotation of a gear wheel 1507 connected to a thread may pull the thread, for example, shortening an effective length of the thread. Optionally, shortening a thread of a pair of threads pulls on the guidewire, deflecting the guidewire distal portion in the direction of the pulled thread.

In some embodiments, multiple thread guidewires may include threads arranged adjacent each other (e.g. lying side by side, optionally connected at a proximal and/or distal end of the guidewire) and/or threads that are arranged coaxially, for example, an inner thread lying within a lumen of an outer thread.

Manipulation of the threads (e.g. by pulling and/or advancing a thread of the double thread arrangement) may deflect the guidewire and/or affect a stiffness of the guidewire distal portion, for example if an inner thread is pulled proximally from the lumen of the outer thread, thereby potentially affecting a rigidity of the guidewire.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An adaptor for coupling a proximal portion of an elongate surgical tool to a motorized robotic surgical device, said elongate surgical tool comprising a distal end and a proximal portion, said proximal portion comprising one or more control components, the adaptor comprising:

a recess shaped and sized for receiving said proximal portion of said elongate surgical tool;

one or more movers positioned to contact and move said one or more control components to affect said distal end of said elongate surgical tool; and transmission coupling which couples said one or more movers to motorized transmission of the robotic surgical device;

wherein at least an inner portion of said adaptor in which said recess is defined is configured to rotate along with the proximal portion of the tool.

2. The adaptor according to claim 1, wherein said proximal portion is a handle of said elongate surgical tool.

3. The adaptor according to claim 1, wherein said affect on said distal end comprises one or more of affecting a stiffness of said distal end, affecting a deflection of said distal end, affecting a rotation of said distal end, affecting expansion of said elongate surgical tool and affecting a deployment of a structure in said elongate surgical tool.

4. The adaptor according to claim 1, wherein manipulation of said proximal portion is coordinated with other manipulations, comprising one or more of linear movement and rotational movement, carried out by said motorized robotic surgical device on said elongate surgical tool.

5. The adaptor according to claim 1, wherein each of said one or more movers is independently actuated via said transmission coupling.

6. The adaptor according to claim 1, wherein said recess is shaped and sized to provide for rotation of said proximal portion about the long axis, while preventing an axial movement and/or lateral movement of said proximal portion within said recess.

7. The adaptor according to claim 1, wherein said one or more movers include an indentation formed in said recess, the indentation shaped and sized to fit onto a control component of the proximal portion of the tool.

8. The adaptor according to claim 1, wherein said one or more control components are from the group of: an axial slider, a lock, a rotatable knob.

9. The adaptor according to claim 1, wherein said recess and said one or more movers are configured to rotate while said transmission coupling remains stationary.

10. The adaptor according to claim 1, comprising at least one sensor configured for indicating a relative position of said one or movers.

11. The adaptor according to claim 1, comprising a housing in which said recess is defined and which includes said one or more movers and said transmission coupling.

12. The adaptor according to claim 11, wherein inner walls of said housing which define said recess are located to prevent movement of a body of said proximal portion within said recess while force is applied to said control elements by said movers of said adaptor.

13. The adaptor according to claim 11, wherein said housing comprises one or more motors which actuate said one or more movers.

14. The adaptor according to claim 11, wherein said housing is configured to be rotated as single unit about a long axis of said recess.

15. The adaptor according to claim 11, wherein said housing comprises mechanical and/or electrical connections positioned and configured to attach to a housing of the robotic surgical device.

16. An adaptor for coupling a proximal portion of an elongate surgical tool to a motorized robotic surgical device, said elongate surgical tool comprising a distal end and a proximal portion, said proximal portion comprising one or more control components, the adaptor comprising:

a recess shaped and sized for receiving said proximal portion of said elongate surgical tool;

one or more movers positioned to contact and move said one or more control components to affect said distal end of said elongate surgical tool;

transmission coupling which couples said one or more movers to motorized transmission of the robotic surgical device;

a housing in which said recess is defined and which includes said one or more movers and said transmission coupling;

wherein said housing is configured to be rotated as single unit about a long axis of said recess.

17. An adaptor for coupling a proximal portion of an elongate surgical tool to a motorized robotic surgical device, said elongate surgical tool comprising a distal end and a proximal portion, said proximal portion comprising one or more control components, the adaptor comprising:

a recess shaped and sized for receiving said proximal portion of said elongate surgical tool;

one or more movers positioned to contact and move said one or more control components to affect said distal end of said elongate surgical tool;

transmission coupling which couples said one or more movers to motorized transmission of the robotic surgical device;

wherein said recess and said one or more movers are configured to rotate while said transmission coupling remains stationary.

18. An adaptor for coupling a proximal portion of an elongate surgical tool to a motorized robotic surgical device, said elongate surgical tool comprising a distal end and a proximal portion, said proximal portion comprising one or more control components, the adaptor comprising:

a recess shaped and sized for receiving said proximal portion of said elongate surgical tool;

one or more movers positioned to contact and move said one or more control components to affect said distal end of said elongate surgical tool;

transmission coupling which couples said one or more movers to motorized transmission of the robotic surgical device;

a housing in which said recess is defined and which includes said one or more movers and said transmission coupling;

wherein said housing comprises mechanical and/or electrical connections positioned and configured to attach to a housing of the robotic surgical device.

* * * * *